US008603481B2

(12) United States Patent
Kawai et al.

(10) Patent No.: US 8,603,481 B2
(45) Date of Patent: Dec. 10, 2013

(54) THERAPEUTIC AGENTS FOR SOLID TUMORS

(75) Inventors: Shigeto Kawai, Kamakura (JP); Masahiko Mihara, Gotenba (JP); Yasuo Koishihara, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 92 days.

(21) Appl. No.: 10/574,860

(22) PCT Filed: Oct. 7, 2004

(86) PCT No.: PCT/JP2004/015205
§ 371 (c)(1), (2), (4) Date: Apr. 6, 2006

(87) PCT Pub. No.: WO2005/034994
PCT Pub. Date: Apr. 21, 2005

(65) Prior Publication Data
US 2007/0110753 A1 May 17, 2007

(30) Foreign Application Priority Data
Oct. 10, 2003 (JP) ................. 2003-352819

(51) Int. Cl.
*A61K 39/395* (2006.01)
(52) U.S. Cl.
USPC ........... 424/174.1; 424/130.1; 424/133.1; 424/141.1; 424/142.1; 424/143.1; 424/144.1; 424/152.1; 424/155.1
(58) Field of Classification Search
None
See application file for complete search history.

(56) References Cited

U.S. PATENT DOCUMENTS

| 6,503,510 B2 * | 1/2003 | Koishihara et al. | 424/156.1 |
| 2001/0051710 A1 * | 12/2001 | Hirano et al. | 530/388.23 |
| 2003/0045691 A1 | 3/2003 | Ono et al. | |
| 2003/0211498 A1 * | 11/2003 | Morin et al. | 435/6 |

FOREIGN PATENT DOCUMENTS

| EP | 0 960 936 A1 * | 1/1999 |
| EP | 0 997 152 A1 | 5/2000 |
| EP | 1 364 657 A1 | 11/2003 |
| JP | 10155494 A | 6/1998 |
| WO | WO 01/62784 A2 | 8/2001 |
| WO | WO 01/75177 A2 | 10/2001 |
| WO | WO 02/064159 A1 | 8/2002 |
| WO | WO 2004/039398 A1 | 5/2004 |

OTHER PUBLICATIONS

Rudikoff, S., Giusti, A.M., Cook, W.D., and Scharff, M.D. Single amino acid substitution altering antigen-binding specificity. Proceedings of the National Academy of Sciences, 1982. vol. 79, pp. 1979-1983.*
Mac Callum, R.M., Martin, A.C.R., and Thornton, J.M. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of 'abbreviated' complementarity-determining regions containing specificity-determining residues essential for ligand contact to engineer a less immunogenic humanized monoclonal antibody. Journal of Immunology, 2002. vol. 169, pp. 3076-3084.*
Casset, F., Roux, F., Mouchet, P., Bes, C., Chardes, T., Granier, C., Mani, J., Pugniere, M., Laune, D., Pau, B., Kaczorek, M., Lahana, R., and Rees, A. A peptide mimetic of an anti-CD4 monoclonal antibody by rational design. Biochemical and Biophysical Research Communications, 2003. vol. 307, pp. 198-205.*
Vajdos, F.F., Adams, C.W., Breece, T.N., Presta, L.G., De Vos, A.M., and Sidhu, S.S. Comprehensive functional maps of the antigen-binding site of an anti-ErbB2 antibody obtained with shotgun scanning mutagenesis. Journal of Molecular Biology, 2002. vol. 320, pp. 415-428.*
Holm, P., Jafari, R., and Sundstrom, B.E. Functional mapping and single chain construction of the anti-cytokeratin 8 monoclonal antibody TS1. Molecular Immunology, 2007. vol. 44, pp. 1075-1084.*
Chen, Y., Wiesmann, C., Fuh, G., Li, B., Christinger, H.W., McKay, P., De Vos, A.M., and Lowman, H.B. Selection and analysis of an optimized anti-VEGF antibody: crystal structure of an affinity matured Fab in complex with antigen. Journal of Molecular Biology, 1999. vol. 293, pp. 865-881.*
Wu, H., Nie, Y., Huse, W.D., and Watkins, J.D. Humanization of a murine monoclonal antibody by simulaneous optimization of framework and CDR residues. Journal of Molecular Biology, 1999. vol. 294, pp. 151-162.*
Freshney, R.I. Culture of Animal Cells, a manual of basic technique. Alan R. Liss, Inc. 1983, New York. p. 4.*
Dermer, G.B. Another anniversary for the war on cancer. Bio/technology, 1994. vol. 12 p. 320.*
Lewin. Genes IV. 1990. Oxford University Press, p. 810.*
Clynes, Towers, Presta, and Ravetch. Inhibitory Fc receptors modulate in vivo cytotoxicity against tumor targets. Nature Medicine, 2000. vol. 6, pp. 443-446.*
Kawai et al, Oncology Reports 2006; 15:361-367.*
Ozaki, et al., "Localization and Imaging of Human Plasmacytoma Xenografts in Severe Combined Immunodeficiency Mice by a New Murine Monoclonal Antibody, Anti-HM1.24", Tokushima J. exp. Med, vol. 43, pp. 7-15 (1996).
Shiku, H., "Antibody therapy for cancer", Second Department of Internal Medicine, Mie University School of Medicine, vol. 20, No. 6 (2002).
Treon, et al., "Immunotherapeutic Strategies for the Treatment of Plasma Cell Malignancies", Chemical Abstracts, Seminars in Oncology, vol. 27, No. 5, pp. 598-613 (2000).
Fujimoto et al., "Regulatory mechanism of nm23-H 1 expression in hepatocellular carcinoma analyzed by several electrophoresis," Jpn. J. Electroph., 1996, 40(313):25-29.
Ropponen et al., "Expression of transcription factor AP-2 in colorectal adenomas and adenocarcinomas; comparison of immunohistochemistry and in situ hybridization," J. Clin. Pathol., 2001, 54:533-538.

* cited by examiner

*Primary Examiner* — Sheela J Huff
*Assistant Examiner* — Jessica H Roark
(74) *Attorney, Agent, or Firm* — Foley & Lardner LLP

(57) ABSTRACT

A therapeutic agent for solid tumors, the agent comprising as an active ingredient, an antibody that specifically binds to a protein having the amino acid sequence represented by SEQ ID NO:2 or an antibody fragment maintaining the antibody activity.

6 Claims, 19 Drawing Sheets

Fig. 1
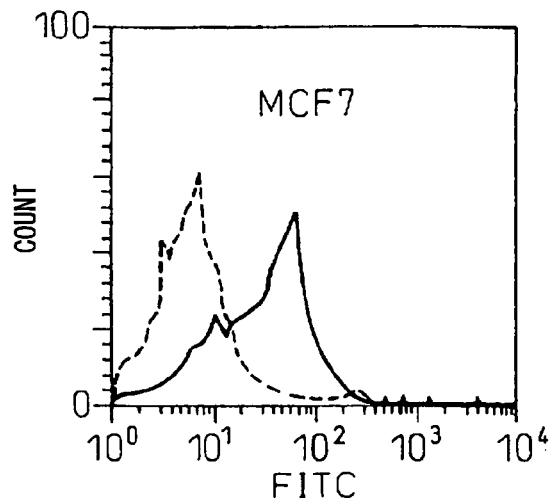
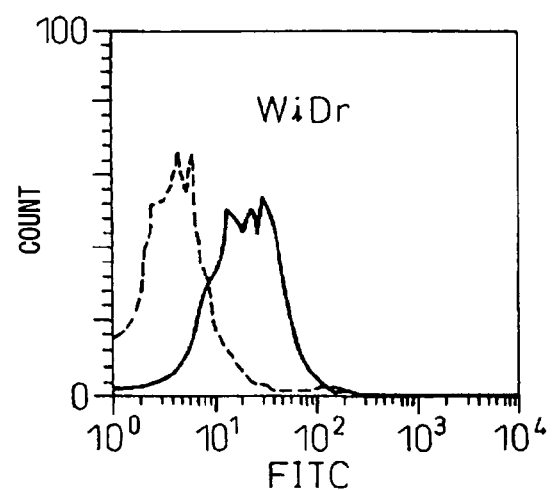
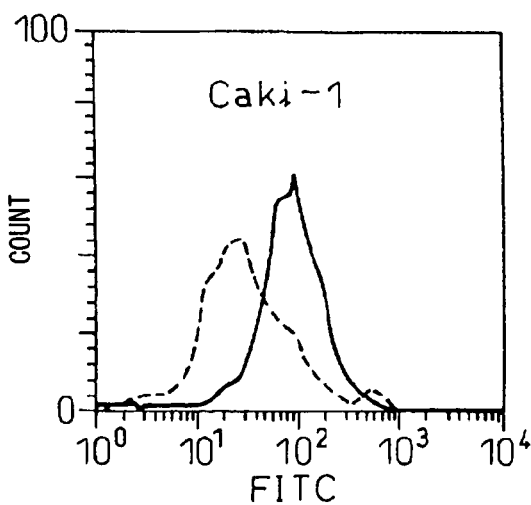

Fig.2
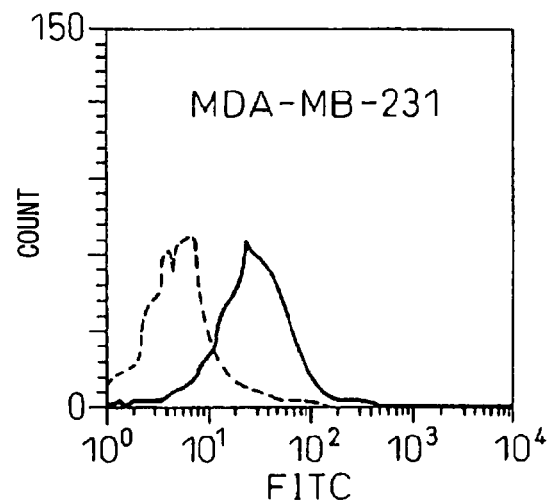
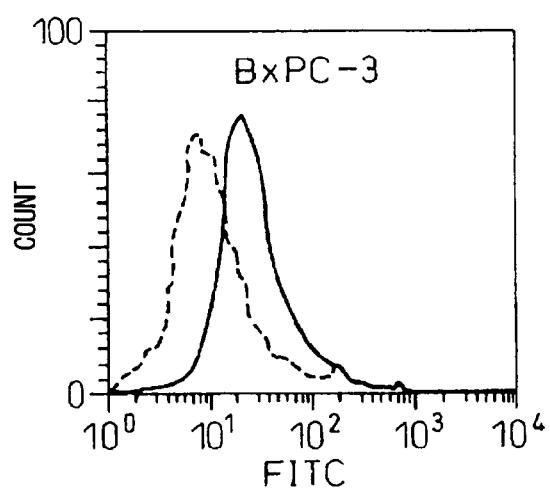
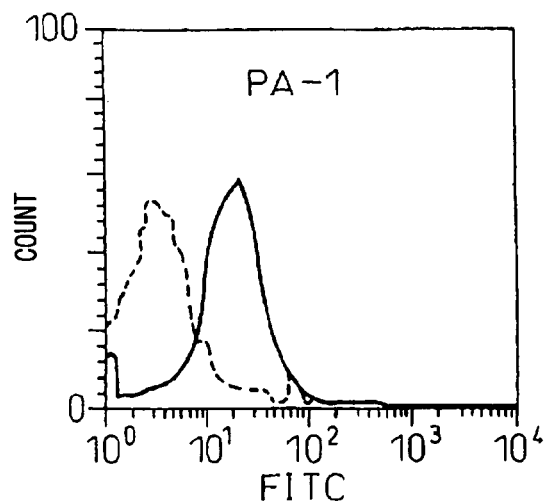

Fig. 3
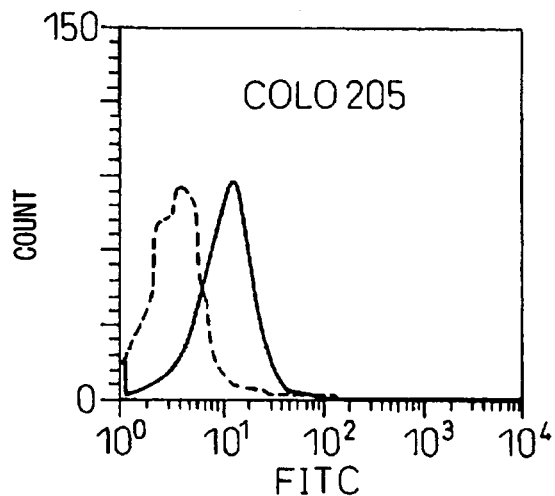
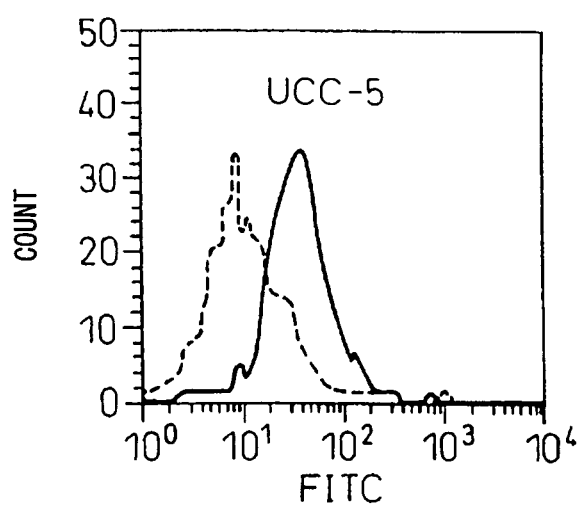

Fig.6

- ⋯△⋯ HM25/HM ANTIBODY-DG44
- ─▲─ HM25/HM ANTIBODY-YB
- ⋯◇⋯ HM31/HM ANTIBODY-DG44
- ─◆─ HM31/HM ANTIBODY-YB
- ⋯□⋯ HM21/HM ANTIBODY-DG44
- ─■─ HM21/HM ANTIBODY-YB
- ⋯○⋯ HM36/HM ANTIBODY-DG44
- ─●─ HM36/HM ANTIBODY-YB

Fig.10
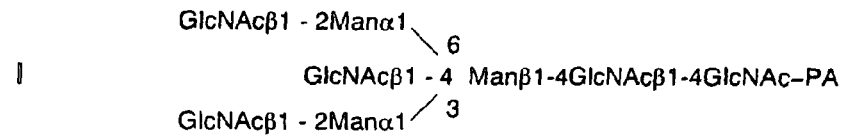
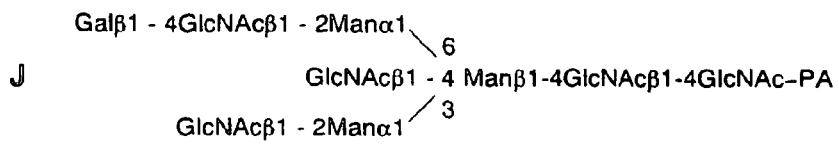
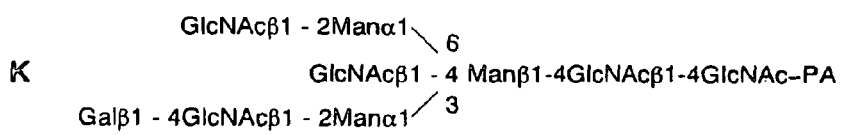
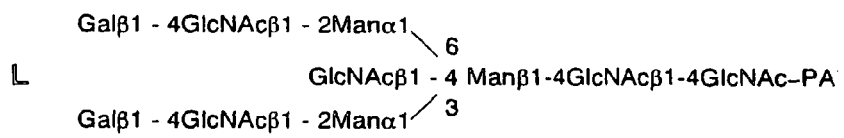
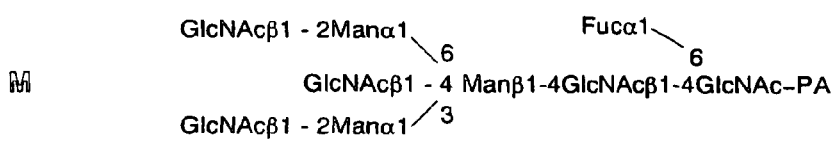
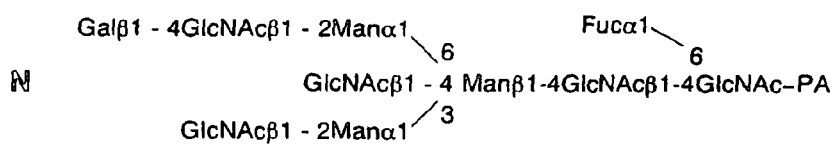
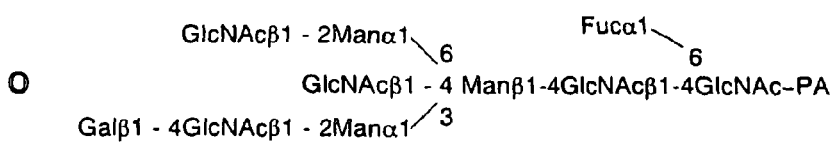
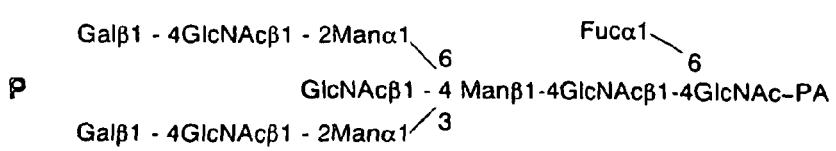

Fig. 14

```
GnTIII mut.nuc   1: ATGAGACGCTACAAGCTCTTTCTCATGTTCTGTATGGCCGGCCTGTGCCTCATCTCCTTC  60
GnTIII ori.nuc   1: ATGAGACGCTACAAGCTCTTTCTCATGTTCTGTATGGCCGGCCTGTGCCTCATCTCCTTC  60
                    ************************************************************

GnTIII mt.nuc   61: CTGCACTTCTTCAAGACCCTGTCCTATGTCACCTTCCCACGAGAACTGGCCTCCCTCAGC 120
GnTIII ori.nuc  61: CTGCACTTCTTCAAGACCCTGTCCTATGTCACCTTCCCCCCCGAGAACTGGCCTCCCTCAGC 120
                    ******************************************* * **************

GnTIII mt.nuc  121: CCTAACCTGGTGTCCAGCTTTTTTCTGGAACAATGCCCCGGTCACGCCCCAGGCCAGCCCT 180
GnTIII ori.nuc 121: CCTAACCTGGTGTCCAGCTTTTTTCTGGAACAATGCCCCGGTCACGCCCCAGGCCAGCCCC 180
                    ***********************************************************

GnTIII mt.nuc  181: GAGCCAGGAGGCCCTGACCTGCTGCGTACCCCACTCTACTCCCACTCGCCCCTGCTGCAG 240
GnTIII ori.nuc 181: GAGCCAGGAGGCCCTGACCTGCTGCGTACCCCACTCTACTCCCACTCGCCCCTGCTGCAG 240
                    ************************************************************

GnTIII mt.nuc  241: CCGCTGCCGCCCAGCAAGGCGGCCGAGGAGCTCCACCGGGTGGACTTGGTGCTGCCCGAG 300
GnTIII ori.nuc 241: CCGCTGCCGCCCAGCAAGGCGGCCGAGGAGCTCCACCGGGTGGACTTGGTGCTGCCCGAG 300
                    ************************************************************
```

Fig. 15

```
GnTIII mt.nuc    301: GACACCACCGAGTATTCGTGCGCACCAAGGCTGGAGGCGTCTGCTTCAAACCCGGCACC  360
GnTIII ori.nuc   301: GACACCACCGAGTATTCGTGCGCACCAAGGCCGGGCGTCTGCTTCAAACCCGGCACC   360
                      ********************************* ** ********************

GnTIII mt.nuc    361: AAGATGCTGGAGAGACCGCCTCCGGGACGACCGGAGGAGAAGCCTGAGGGGCCAACGGA  420
GnTIII ori.nuc   361: AAGATGCTGGAGAGACCGCCGCCCCCGGGACGCCGGAGGAGAAGCCTGAGGGGCCAACGGC  420
                      ******************** ** ** *****  **************************

GnTIII mt.nuc    421: TCCTCGGCCCGGCGACCACCCCGGTACCTCCTGAGCGCCCGGAGCGCACGGGGGCCGA  480
GnTIII ori.nuc   421: TCCTCGGCCCGGCGACCACCCCGGTACCTCCTGAGCGCCTGGCACGCACGGGGGCCGA  480
                      ***************************************  * **************

GnTIII mt.nuc    481: GGTGCACGACGCAAGTGGGTGAGTGCGTGTCTGCCCGGATGGCACGGACCCAGCTGC   540
GnTIII ori.nuc   481: GGCGCCCCGGCCAAGTGGGTGAGTGCGTGTGCCTGCCGGCTGGCACGGACCCAGCTGC  540
                      **  **   ** ******************  * ******  ****************

GnTIII mt.nuc    541: GGCCGTGCCCACTGTGGTGCAGTATTCCAACCTGCCTACCAAGGAGCGGCTGGTGCCCAGG  600
GnTIII ori.nuc   541: GGCCGTGCCCACTGTGGTGCAGTACTCCAACCTGCCCACCAAGGAGCGGCTGGTGCCCAGG  600
                      ************************ *********** **********************
```

Fig. 16

```
GnTIII mt.nuc   601: GAGGTGCCGCGGCCGCGTCATTAATGCTATCAACGTCAACCACGAGTTCGACCTGCTGGAC  660
GnTIII ori.nuc  601: GAGGTGCCGCGGCCGCGTCATCAACGCCATCAACGTCAACCACGAGTTCGACCTGCTGGAC  660
                     *********************  *  **  ** ******************************

GnTIII mt.nuc   661: GTGCGCTTCCACGAGCTGGGCGACGTGGTGGACGCCCTTTGTGGTGTGCGAGTCCAACTTC  720
GnTIII ori.nuc  661: GTGCGCTTCCACGAGCTGGGCGACGTGGTGGACGCCCTTTGTGTGTGCGAGTCCAACTTC  720
                     ******************************************* ** ***************

GnTIII mt.nuc   721: ACGGCTTATGGGAGCCGCGGCCGCTCAAGTTCCGGGAGATGCTGACCAATGGCACCTTC   780
GnTIII ori.nuc  721: ACGGCTTATGGGAGCCGCGGCCGCTCAAGTTCCGGGAGATGCTGACCAATGGCACCTTC   780
                     *************************************************************

GnTIII mt.nuc   781: GAGTACACATCCGCCCACAAGGTGCTCTATGTCTTCCTGGACCACTTTCCTCCTGGAGGACGA  840
GnTIII ori.nuc  781: GAGTACATCCGCCCACAAGGTGCTCTATGTCTTCCTGGACCACTTCCCGCCGGGGGCCGG   840
                     ******* ***********************************   **  **   **

GnTIII mt.nuc   841: CAAGATGGATGGATCGCCGACGACTACCTGCGCACCTTCCTCACCCAGGACGGCGTCTCG  900
GnTIII ori.nuc  841: CAGGACGGCTGGATCGCCGACGACTACCTGCGCACCTTCCTCACCCAGGACGGCGTCTCG  900
                     ** **  ***  ***********************************************
```

Fig. 17

```
GnTIII mt.nuc   901:CGGCTGCGCAACCTGCGGCCCGACGACGTCTTCATCATTGACGATGCGGACGAGATCCCG 960
GnTIII ori.nuc  901:CGGCTGCGCAACCTGCGGCCCGACGACGTCTTCATCATTGACGATGCGGACGAGATCCCG 960
                    ************************************************************

GnTIII mt.nuc   961:GCCCGTGACGGCGTCCTGTTCCTCAAGCTCTACGATGGCTGGACCGAGCCCTTCGCCTTC 1020
GnTIII ori.nuc  961:GCCCGTGACGGCGTCCTTTCCTCAAGCTCTACGATGGCTGGACCGAGCCCTTCGCCTTC 1020
                    ***************** ******************************************

GnTIII mt.nuc  1021:CACATGCGCACGTCGCTCTACGGATTCTTTTGGAAGCAACCGGGCACCCTGGAGGTGGTG 1080
GnTIII ori.nuc 1021:CACATGCGCACGTCGCTCTACGGCTTCTTCTGGAAGCAGCCGGGCACCCTGGAGGTGGTG 1080
                    *********************** ****** ******* *********************

GnTIII mt.nuc  1081:TCAGGCTGCACGGTGGACATGCTGCAGGCAGTGTATGGCTGGACGGCATCCGCCTGCGC 1140
GnTIII ori.nuc 1081:TCAGGCTGCACGGTGGACATGCTGCAGGCAGTGTATGGGCTGGACGGCATCCGCCTGCGC 1140
                    ************************************** *********************

GnTIII mt.nuc  1141:CGCCGCCAATACTACACCATGCCCAACTTCAGACAGTATGAGAACCGCACCGGACACATC 1200
GnTIII ori.nuc 1141:CGCCGCCAGTACTACACCATGCCCAACTTCAGACAGTATGAGAACCGCACCGGCCACATC 1200
                    ******** ******************************************** ******
```

Fig.18

```
GnTIII mt.nuc  1201: CTGGTGCAGTGGTCGCTGGGCAGCCCCCTTCACTTCGCCGGCTGGCACTGCTCCTGGTGC 1260
GnTIII ori.nuc 1201: CTGGTGCAGTGGTCGCTGGGCAGCCCCCTGCACTTCGCCGGCTGGCACTGCTCCTGGTGC 1260
                    ****************************** *****************************

GnTIII mt.nuc  1261: TTCACGCCCGAGGGCATCTACTTCAAGCTCGTGTCCGCCCAGAATGGCGACTTCCCACGC 1320
GnTIII ori.nuc 1261: TTCACGCCCGAGGGCATCTACTTCAAGCTCGTGTCCGCCCAGAATGGCGACTTCCCACGC 1320
                    ************************************************************

GnTIII mt.nuc  1321: TGGGGTGACTACGAGGACAAGCGGGACCTGAACTACATCCGCGGCCTGATCCGCACCGGG 1380
GnTIII ori.nuc 1321: TGGGGTGACTACGAGGACAAGCGGGACCTGAACTACATCCGGGCCTGATCCGCACCGGG 1380
                    ***************************************** *****************

GnTIII mt.nuc  1381: GGCTGGTTCGACGGCACGCAGCAGGAGTACCCGCTGCAGACCCCAGCGAGCACATGTAT 1440
GnTIII ori.nuc 1381: GGCTGGTTCGACGGCACGCAGCAGGAGTACCCGCTGCAGACCCCAGCGAGCACATGTAT 1440
                    ************************************************************

GnTIII mt.nuc  1441: GCGCCCAAGTACCTGCTGAAGAACTACGACCGGTTCCACTACCTTCTGGACAACCCCTAC 1500
GnTIII ori.nuc 1441: GCGCCCAAGTACCTGCTGAAGAACTACGACCGGTTCCACTACCTGGACAACCCCTAC 1500
                    *********************************************** **********
```

Fig.19

```
GnTIII mt.nuc  1501: CAGGAGCCCAGGAGCACGGCTGCGGGAGGATGGGCGCCACAGGGGTCCTGAAGGAAGACCG 1560
GnTIII ori.nuc 1501: CAGGAGCCCAGGAGCACGGCTGCGGGTGGGGGGGTCCCACAGGGGTCCCGAGGGAAGGCCG 1560
                    ************************** **   ******** ***** ** ****** **

GnTIII mt.nuc  1561: CCTGCTCGGGGAAAACTGGACGAGGCGGAAGTCTAG 1596
GnTIII ori.nuc 1561: CCCGCCCGGGGCAAACTGGACGAGGCGGAAGTCTAG 1596
                    ** ** ***** ************************
```

THERAPEUTIC AGENTS FOR SOLID TUMORS

TECHNICAL FIELD

The present invention relates to therapeutic agents for solid tumors (excluding hematopoietic tumors such as malignant lymphoma) comprising, as an active ingredient, an antibody that specifically binds to a protein expressed in said solid tumors. The present invention also relates to an antibody that specifically binds to a protein expressed in solid tumors and that has a cytotoxic activity.

BACKGROUND ART

HM1.24 antigen was discovered as a membrane protein that is highly expressed in human myeloma cells. Then, it was demonstrated that a monoclonal antibody (anti-HM1.24 antibody) that was obtained from a mouse immunized with a human myeloma cell KPC-32 binds to human myeloma cells and plasma cells, and an antigen (HM1.24 antigen) that is recognized by the antibody is highly expressed in human myeloma cell lines such as RPMI8226 (Goto T. et al., Blood (1994), 84, 1922). It has also been reported that an anti-tumor effect can be obtained by the simultaneous administration of anti-HM1.24 antibody to a mouse that underwent the grafting of the human myeloma cell RPMI8226. Thereafter, the cDNA of HM1.24 antigen was obtained and the nucleotide sequence was determined, which revealed that the molecule was identical with Bst2 that had been reported to be a protein expressed in medullary stromal cells (Ishikawa, J. et al., Genomics (1995) 26, 527; International Patent Publication WO 95/10536).

On the other hand, in lymphatic tumors other than myeloma, it was found that HM1.24 antigen was expressed and that anti-HM1.24 antibody exhibits a cytotoxic activity based on antibody-dependent cell-mediated cytotoxicity (ADCC activity) and on complement-dependent cytotoxicity (CDC activity) and exhibits anti-tumor effect against lymphatic tumors (International Patent Publication WO 98/35698). It has also been demonstrated that the stimulation of hematopoietic tumors with interferon α or γ leads to an increase in the amount of HM1.24 antigen expressed, thereby enhancing the anti-tumor effect of anti-HM1.24 antibody (International Patent Publication WO 02/64159).

However, though the expression of HM1.24 antigen in hematopoietic tumors had been noted, its expression in solid tumors such as lung cancer, breast cancer and colon cancer was not known, nor was it known that it can damage solid tumor cells by ADCC.

As solid tumors except for hematopoietic tumors, there can be mentioned head and neck cancer, small cell lung cancer, non-small cell lung cancer (including squamous-cell carcinoma, adenocarcinoma, large cell carcinoma, adenosquamous carcinoma, and polymorphic sarcomatoid cancer, or cancer containing sarcoma components etc.), esophageal cancer, breast cancer, gastric cancer, colon cancer, rectal cancer, hepatic cancer, biliary tract cancer, pancreatic cancer, ovarian cancer, cervical cancer, endometrial cancer, prostate cancer, kidney cancer, bladder cancer, skin cancer, brain tumor, pediatric solid tumor, malignant bone tumor and the like.

Due to recent advances in medical technology, new therapeutic regimens have been proposed and attempted for these solid tumors, but they provide little therapeutic effect on solid tumor in the progressive stage and are still inadequate.

DISCLOSURE OF THE INVENTION

Therapies currently employed for the treatment of solid tumors include, in addition to the surgical removal of the lesion per se, various chemotherapeutic regimens, radiation therapies, bone marrow transplantation and the like, and multidisciplinary treatments combining them are intended to prolong the survival period and to improve QOL. As mentioned above, however, no therapeutic regimens are sufficient, and thus there is a long-standing need for epoch-making therapeutic agents or therapeutic regimens that can prolong the survival of patients. Thus, it is an object of the present invention to provide a new therapeutic agent for solid tumors excluding hematopoietic tumors.

After intensive and extensive research, such as flow cytometry analysis that investigates the amount expressed in solid tumor cells, and the determination of cytotoxic activity such as ADCC activity and CDC activity, etc. using anti-HM1.24 antibody in order to provide such therapeutic agents, the present inventors have found that the antigen protein that anti-HM1.24 antibody recognizes is expressed in various solid tumors in addition to hematopoietic tumors, and that anti-HM1.24 antibody has an anti-tumor effect on solid tumors, and thereby have completed the present invention.

Thus, the present invention provides a therapeutic agent for solid tumors, said agent comprising as an active ingredient an antibody that specifically binds to a protein having the amino acid sequence as set forth in SEQ ID NO: 2 and that has a cytotoxic activity.

The above antibody may preferably be a monoclonal antibody, a chimeric antibody comprising the constant region of a human antibody and the variable region of a mouse antibody, a humanized antibody comprising the complementarity determining region of a mouse antibody and the framework region and the constant region of a human antibody, or an antibody in which all of the complementarity determining region, the framework region and the constant region are derived from a human antibody.

The above antibody may be an antibody in which a sugar chain has been altered.

The fragments of the above antibody may be, for example, Fab, Fab', F(ab')$_2$, or Fv fragments.

The above solid tumors are for example head and neck cancer, small cell lung cancer, non-small cell lung cancer (including squamous-cell carcinoma, adenocarcinoma, large cell carcinoma, adenosquamous carcinoma, and polymorphic sarcomatoid cancer, or cancer containing sarcoma components etc.), esophageal cancer, breast cancer, gastric cancer, colon cancer, rectal cancer, hepatic cancer, biliary tract cancer, pancreatic cancer, ovarian cancer, cervical cancer, endometrial cancer, prostate cancer, kidney cancer, bladder cancer, skin cancer, brain tumor, pediatric solid tumor, malignant bone tumor, and metastatic cancers of these solid tumors.

BRIEF EXPLANATION OF THE DRAWINGS

FIG. 1 is a graph showing the reactivity of humanized anti-HM1.24 antibody with human solid tumor cell lines (MCF7, WiDr and Caki-1). The solid line represents a sample that was reacted with the humanized anti-HM1.24 antibody and the dotted line represents a sample that was reacted with fluorescently labelled human IgG1.

FIG. 2 is a graph showing the reactivity of humanized anti-HM1.24 antibody with human solid tumor cell lines (MDA-MB-231, BxPc-3 and PA-1). The solid line represents a sample that was reacted with the humanized anti-HM1.24 antibody and the dotted line represents a sample that was reacted with fluorescently labelled human IgG1.

FIG. 3 is a graph showing the reactivity of humanized anti-HM1.24 antibody with human solid tumor cell lines (COLO 205 and UCC-5). The solid line represents a sample that was reacted with the humanized anti-HM1.24 antibody and the dotted line represents a sample that was reacted with fluorescently labelled human IgG1.

FIG. 6 is a result of ADCC activity of human PBMC at each antibody concentration of HM1.24 antibody-DG44 and HM1.24 antibody-YB with E/T ratio=25 using four HM1.24 antigen-expressing CHO cells (HM26, HM31, HM21, HM36) as the target cell.

FIG. 10 shows the structures of sugars I-P as shown in FIG. 8 and Table 1.

FIG. 14 shows a comparison of a nucleotide sequence (SEQ ID NO: 30) (GnTIII ori.nuc) that encodes the native human GnTIII and a nucleotide sequence (SEQ ID NO: 31) (GnTIII mut.nuc) that encodes a mutant human GnTIII. In the figure, the asterisk indicates that the corresponding bases in both sequences are identical.

FIG. 15 shows a comparison of a nucleotide sequence (SEQ ID NO: 30) (GnTIII ori.nuc) that encodes the native human GnTIII and a nucleotide sequence (SEQ ID NO: 31) (GnTIII mut.nuc) that encodes a mutant human GnTIII. In the figure, the asterisk indicates that the corresponding bases in both sequences are identical.

FIG. 16 shows a comparison of a nucleotide sequence (SEQ ID NO: 30) (GnTIII ori.nuc) that encodes the native human GnTIII and a nucleotide sequence (SEQ ID NO: 31) (GnTIII mut.nuc) that encodes a mutant human GnTIII. In the figure, the asterisk indicates that the corresponding bases in both sequences are identical.

FIG. 17 shows a comparison of a nucleotide sequence (SEQ ID NO: 30) (GnTIII ori.nuc) that encodes the native human GnTIII and a nucleotide sequence (SEQ ID NO: 31) (GnTIII mut.nuc) that encodes a mutant human GnTIII. In the figure, the asterisk indicates that the corresponding bases in both sequences are identical.

FIG. 18 shows a comparison of a nucleotide sequence (SEQ ID NO: 30) (GnTIII ori.nuc) that encodes the native human GnTIII and a nucleotide sequence (SEQ ID NO: 31) (GnTIII mut.nuc) that encodes a mutant human GnTIII. In the figure, the asterisk indicates that the corresponding bases in both sequences are identical.

FIG. 19 shows a comparison of a nucleotide sequence (SEQ ID NO: 30) (GnTIII ori.nuc) that encodes the native human GnTIII and a nucleotide sequence (SEQ ID NO: 31) (GnTIII mut.nuc) that encodes a mutant human GnTIII. In the figure, the asterisk indicates that the corresponding bases in both sequences are identical.

BEST MODE FOR CARRYING OUT THE INVENTION

Figure 4:
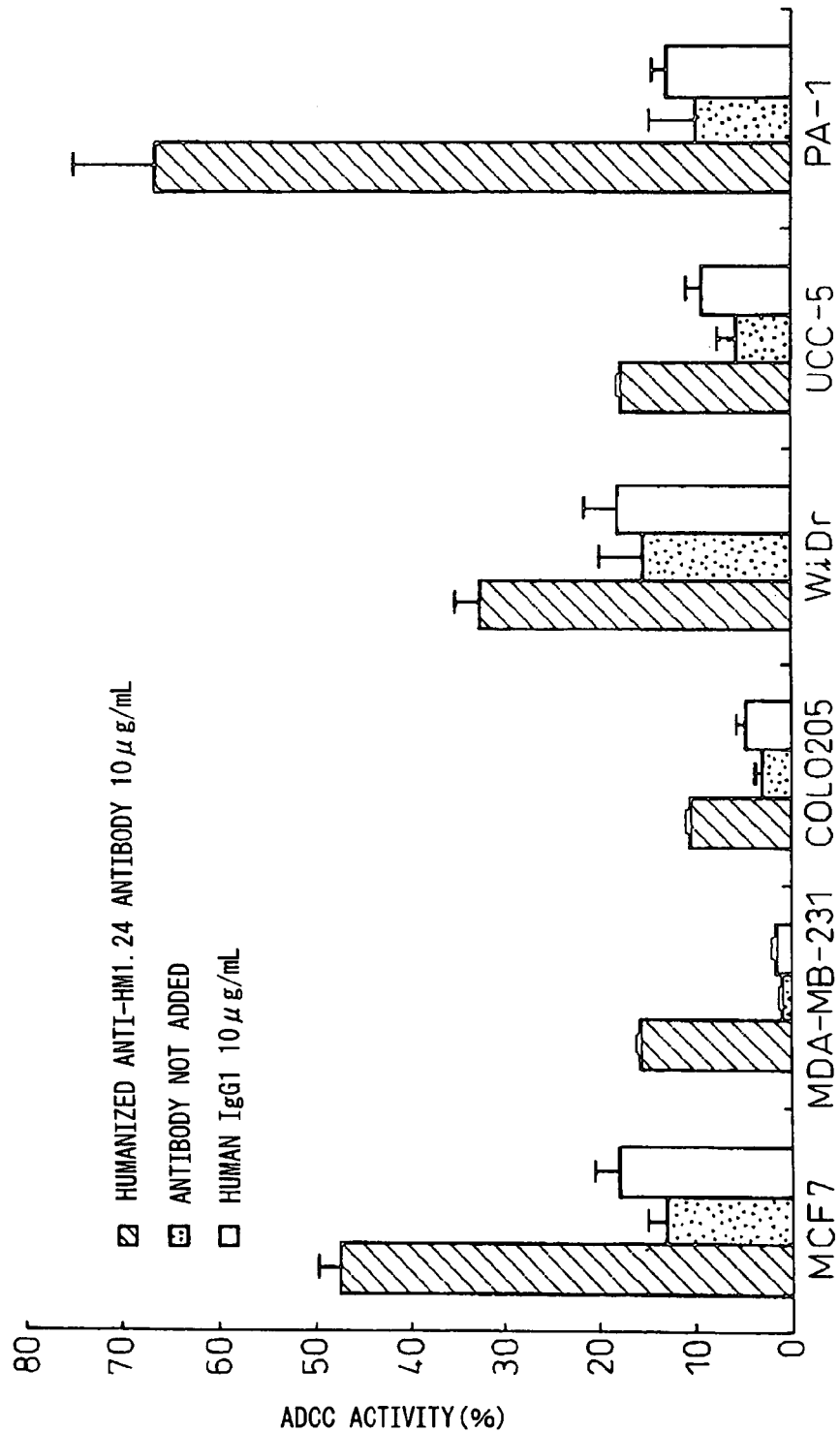
FIG. 4 is a graph showing the ADCC activity of humanized anti-HM1.24 antibody to human solid tumor cell lines.

The present inventors have demonstrated for the first time that HM1.24 antigen is expressed in solid tumors other than hematopoietic tumors and that anti-HM1.24 antibody exhibits a cytotoxic activity via ADCC etc. As used herein, cells to which anti-HM1.24 antibody exhibits a anti-tumor effect are HM1.24 antigen-expressing solid tumors other than hematopoietic tumors, and specifically there can be mentioned head and neck cancer, small cell lung cancer, non-small cell lung cancer (including squamous-cell carcinoma, adenocarcinoma, large cell carcinoma, adenosquamous carcinoma, and polymorphic sarcomatoid cancer, or cancer containing sarcoma components etc.), esophageal cancer, breast cancer, gastric cancer, colon cancer, rectal cancer, hepatic cancer, biliary tract cancer, pancreatic cancer, ovarian cancer, cervical cancer, endometrial cancer, prostate cancer, kidney cancer, bladder cancer, skin cancer, brain tumor, pediatric solid tumor, malignant bone tumor and the like. There can also be mentioned metastasis and metastatic lesions of these solid tumors, and carcinomatous pleuritis, cancerous peritonitis and cancerous meningitis etc. associated with solid tumors.

Antibodies for use in the present invention are now explained. The antibody may be monoclonal or polyclonal antibody, and preferably are monoclonal antibody. Then methods of preparing monoclonal antibody will be described.
Hybridoma The hybridoma produced by the antibody for use in the present invention can be basically constructed using a known technology as described below. Thus, HM1.24 antigen protein or a HM1.24 antigen-expressing cell may be used as an immunizing antigen and is immunized in the conventional method of immunization. The immune cells thus obtained are fused with known parent cells in the conventional cell fusion process, and then monoclonal antibody-producing cells are screened by the conventional screening method to construct the desired hybridoma.

Specifically, monoclonal antibody may be obtained in the following manner. For example, as the cell expressing HM1.24 antigen which is the immunizing antigen to obtain antibody, a human multiple myeloma cell line KPMM2 (Japanese Unexamined Patent Publication (Kokai) No. 7-236475) and KPC-32 (Goto, T. et al., Jpn. J. Clin. Hematol.

(1991) 32, 1400) can be used. As the immunizing antigen, it is also possible to use a protein having the amino acid sequence as set forth in SEQ ID NO: 2 or a peptide or a polypeptide containing an epitope recognized by anti-HM1.24 antibody.

The cDNA of the protein having the amino acid sequence as set forth in SEQ ID NO: 2 used as the immunizing antigen is inserted into the XbaI cleavage site of the pUC19 vector to prepare a plasmid pRS38-pUC19. *E. coli* having the plasmid pRS38-pUC19 has been internationally deposited under the provisions of the Budapest Treaty as *Escherichia coli* DH5α (pRS38-pUC19) on Oct. 5, 1993 with the Patent Microorganism Depository of the National Institute of Industrial Science and Technology, of Chuo Dai 6, 1-1, Higashi 1-chome, Tsukuba city, Ibaraki Pref., Japan, as FERM BP-4434 (Japanese Unexamined Patent Publication (Kokai) No. 7-196694). Using the cDNA fragment contained in this plasmid pRS38-pUC19, a peptide or a polypeptide that contains an epitope recognized by anti-HM1.24 antibody can be constructed by a gene engineering technology.

Mammals to be immunized with the immunizing antigen are not specifically limited, and they are preferably selected in consideration of their compatibility with the parent cell for use in cell fusion. They generally include rodents such as mice, rats, and hamsters.

Immunization of animals with an immunizing antigen is carried out using a known method. A general method, for example, involves the intraperitoneal or subcutaneous injection of an immunizing antigen to the mammal.

Specifically, an immunizing antigen which has been diluted and suspended in an appropriate amount of phosphate buffered saline (PBS) or saline etc. is mixed, as desired, with an appropriate amount of a common adjuvant, for example Freund's complete adjuvant. After being emulsified, it is preferably administered to the mammal several times every 4 to 21 days. Alternatively, a suitable carrier may be used at the time of immunization with the immunizing antigen.

After immunizing in this manner and confirming the increase in the desired antibody levels in the serum, immune cells are harvested from the mammal and are subjected to cell fusion. Preferably, as immune cells subjected to cell fusion, splenocytes may be specifically mentioned.

The mammalian myeloma cells as the other parent cells which are subjected to cell fusion with the above-mentioned immune cells preferably include various known cell lines such as P3X63Ag8.653 (J. Immunol. (1979) 123: 1548-1550), P3X63Ag8U.1 (Current Topics in Microbiology and Immunology (1978) 81: 1-7), NS-1 (Kohler, G. and Milstein, C., Eur. J. Immunol. (1976) 6: 511-519), MPC-11 (Margulies, D. H. et al., Cell (1976) 8: 405-415), SP2/0 (Shulman, M. et al., Nature (1978) 276: 269-270), FO (de St. Groth, S. F. et al. J. Immunol. Methods (1980) 35: 1-21), S194 (Trowbridge, I. S., J. Exp. Med. (1978) 148: 313-323), R210 (Galfre, G. et al., Nature (1979) 277: 131-133) and the like.

Cell fusion between the above immune cells and the myeloma cells may be essentially conducted in accordance with a known method such as is described in Milstein et al. (Kohler, G. and Milstein, C., Methods Enzymol. (1981) 73: 3-46) and the like.

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used, and, in addition, an adjuvant such as dimethyl sulfoxide may be added as desired to enhance the efficiency of the fusion.

The preferred ratio of the immune cells and the myeloma cells to be used is, for example, 1 to 10 times more immune cells than the myeloma cells. Examples of culture media to be used for the above cell fusion include RPMI1640 medium and MEM culture medium suitable for the growth of the above myeloma cell lines, and the conventional culture medium used for this type of cell culture, and besides a serum supplement such as fetal calf serum (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of about 1000 to 6000, is added at a concentration of 30 to 60% (w/v), and mixed to obtain the desired fusion cells (hybridomas). Then, by repeating the sequential addition of a suitable culture liquid and centrifugation to remove the supernatant, cell fusion agents etc. which are undesirable for the growth of the hybridoma can be removed.

Said hybridoma is selected by culturing in a conventional selection medium, for example, the HAT culture medium (a culture liquid containing hypoxanthine, aminopterin, and thymidine). Culturing in said HAT culture medium is continued generally for a period of time sufficient to effect killing of the cells (non-fusion cells) other than the desired hybridoma, generally several days to several weeks. Then, the conventional limiting dilution method is conducted in which the hybridomas that produce the desired antibody are screened and cloned.

In addition to obtaining the above hybridoma by immunizing an animal other than the human with an antigen, it is also possible to sensitize human lymphocytes in vitro with HM1.24 antigen or HM1.24 antigen-expressing cells, and to allow the resulting sensitized lymphocytes to be fused with a human myeloma cell, for example U266, and thereby to obtain the desired human antibody having the activity of binding HM1.24 antigen or HM1.24 antigen-expressing cells (see Japanese Examined Patent Publication (Kokoku) No. 1-59878). Furthermore, a transgenic animal having the entire repertoire of human antibody genes is immunized with HM1.24 antigen or HM1.24 antigen-expressing cells to obtain the desired human antibody according to the above-mentioned method (see International Patent Application WO 93/12227, WO 92/03918, WO 94/02602, WO 94/25585, WO 96/34096, and WO 96/33735).

Furthermore, using a human antibody library, the desired human antibody can also be isolated by panning. For example, the variable region of a human antibody may be expressed as a single chain antibody (scFv) by the phage display method on the surface of phages, and then phages binding to HM1.24 antigen can be selected using a HM1.24 antigen-immobilized plate. By analyzing the genes of the selected phages, genes encoding the variable region of antibody that binds to HM1.24 antigen can be identified. Using these gene sequences, human anti-HM1.24 antibody can be prepared. These methods are known and may be referenced in WO 92/01047, WO 92/20791, WO 93/06213, WO 93/11236, WO 93/19172, WO 95/01438, and WO 95/15388.

The monoclonal antibody-producing hybridomas thus constructed can be subcultured in the conventional culture liquid, or can be stored for a prolonged period of time in liquid nitrogen.

In order to obtain monoclonal antibodies from said hybridoma, there may be employed a method in which said hybridoma is cultured in the conventional method and the antibodies are obtained as the culture supernatant, or a method in which the hybridoma is administered to and grown in a mammal compatible with said hybridoma and the antibodies are obtained as the ascites, or other methods. The former method is suitable for obtaining high-purity antibodies, whereas the latter is suitable for a large scale production of antibodies.

Monoclonal Antibody

Specifically the anti-HM1.24 antibody-producing hybridoma can be constructed using the method of Goto, T. et al. (Blood (1994) 84: 1922-1930). It can be conducted by: a method in which the anti-HM1.24 antibody-producing hybridoma that was internationally deposited under the provisions of the Budapest Treaty as FERM BP-5233 on Apr. 27, 1995 with the Patent Microorganism Depository of the National Institute of Industrial Science and Technology, of Chuo Dai 6, 1-1, Higashi 1-chome, Tsukuba city, Ibaraki Pref., Japan, is intraperitoneally injected to BALB/c mice (bred by CLEA Japan) to obtain the ascites, from which the anti-HM1.24 antibody is purified; or a method in which said hybridoma is cultured in a suitable culture medium such as the RPMI1640 medium containing 10% bovine fetal serum and 5% BM-Condimed H1 (manufactured by Boehringer Mannheim), the hybridoma SFM medium (manufactured by GIBCO-BRL), the PFHM-II medium (manufactured by GIBCO-BRL) and the like, and the anti-HM1.24 antibody can be purified from the supernatant.

Recombinant Antibody

A recombinant antibody which was produced by the recombinant gene technology in which an antibody gene was cloned from the hybridoma and integrated into a suitable vector which was then introduced into a host can be used in the present invention as monoclonal antibody (see, for example, Carl, A. K., Borrebaeck, and James, W. Larrick, THERAPEUTIC MONOCLONAL ANTIBODIES, published in the United Kingdom by MACMILLAN PUBLISHERS LTD., 1990).

Specifically, mRNA encoding the variable region (V) of the desired antibody is isolated from the hybridoma producing the antibody. The isolation of mRNA is conducted by preparing total RNA using, for example, a known method such as the guanidine ultracentrifuge method (Chirgwin, J. M. et al., Biochemistry (1979) 18, 5294-5299), the AGPC method (Chmczynski, P. et al., (1987) 162, 156-159), and then mRNA is purified from the total RNA using the mRNA Purification kit (manufactured by Pharmacia) and the like. Alternatively, mRNA can be directly prepared using the QuickPrep mRNA Purification Kit (manufactured by Pharmacia).

cDNA of the V region of the antibody may be synthesized from the mRNA thus obtained using a reverse transcriptase. cDNA may be synthesized using the AMV Reverse Transcriptase First-strand cDNA Synthesis Kit and the like. Alternatively, for the synthesis and amplification of cDNA, the 5'-Ampli FINDER RACE Kit (manufactured by Clontech) and the 5'-RACE method (Frohman, M. A. et al., Proc. Natl. Acad. Sci. U.S.A. (1988) 85, 8998-9002; Belyavsky, A. et al., Nucleic Acids Res. (1989) 17, 2919-2932) that employs PCR may be used. The desired DNA fragment is purified from the PCR product obtained and may be ligated to vector DNA. Moreover, a recombinant vector is constructed therefrom and then is introduced into E. coli etc., from which colonies are selected to prepare the desired recombinant vector. The nucleotide sequence of the desired DNA may be confirmed by a known method such as the dideoxy method.

Once the DNA encoding the V region of the desired antibody has been obtained, it may be ligated to DNA encoding the constant region (C region) of the desired antibody, which is then integrated into an expression vector. Alternatively, the DNA encoding the V region of the antibody may be integrated into an expression vector which already contains DNA encoding the C region of the antibody.

In order to produce the antibody for use in the present invention, the antibody gene is integrated, as described below, into an expression vector so as to be expressed under the control of the expression regulatory region, for example an enhancer and/or a promoter. Subsequently, the expression vector may be transformed into a host cell and the antibody can then be expressed therein.

Altered Antibody

In accordance with the present invention, artificially altered recombinant antibody such as chimeric antibody and humanized antibody can be used for the purpose of lowering heterologous antigenicity against humans. These altered antibody can be produced using known methods.

Chimeric antibody can be obtained by ligating the thus obtained DNA encoding the V region of antibody to DNA encoding the C region of human antibody, which is then integrated into an expression vector and introduced into a host for production of the antibody therein (see European Patent Application EP 125023, and International Patent Application WO 96/02576). Using this known method, chimeric antibody useful for the present invention can be obtained.

For example, E. coli having the plasmid that contains the L chain and the H chain of chimeric anti-HM1.24 antibody has been internationally deposited under the provisions of the Budapest Treaty as Escherichia coli DH5α (pUC19-1.24L-gκ) and Escherichia coli DH5α (pUC19-1.24H-gγ1), respectively, on Aug. 29, 1996 with the Patent Microorganism Depository of the National Institute of Industrial Science and Technology, of Chuo Dai 6, 1-1, Higashi 1-chome, Tsukuba city, Ibaraki Pref., Japan, as FERM BP-5646 and FERM BP-5644, respectively (see International Patent Application WO 98/14580).

Humanized antibody, which is also called reshaped human antibody, has been made by transplanting the complementarity determining region (CDR) of antibody of a mammal other than the human, for example mouse antibody, into the CDR of human antibody. The general recombinant DNA technology for preparation of such antibodies is also known (see European Patent Application EP 125023 and International Patent Application WO 96/02576).

Specifically, a DNA sequence which was designed to ligate the CDR of mouse antibody with the framework region (FR) of human antibody is synthesized by the PCR method with several divided oligonucleotides having sections overlapping with one another at the ends thereof. The DNA thus obtained is ligated to the DNA encoding the C region of human antibody and then is integrated into an expression vector, which is introduced into a host for antibody production (see European Patent Application EP 239400 and International Patent Application WO 96/02576).

For the FR of human antibody ligated through CDR, the complementarity determining region that forms a favorable antigen binding site is selected. When desired, amino acids in the framework region of the antibody variable region may be substituted so that the complementarity determining region of reshaped human antibody may form an appropriate antigen biding site (Sato, K. et al., Cancer Res. (1993) 53, 851-856).

For example, E. coli having the plasmid that contains the L chain and the H chain of humanized anti-HM1.24 antibody has been internationally deposited under the provisions of the Budapest Treaty as Escherichia coli DH5α (pUC19-RVLa-AHM-gκ) and Escherichia coli DH5α (pUC19-RVHr-AHM-gγ1), respectively, on Aug. 29, 1996 with the Patent Microorganism Depository of the National Institute of Industrial Science and Technology, of Chuo Dai 6, 1-1, Higashi 1-chome, Tsukuba city, Ibaraki Pref., Japan, as FERM BP-5645 and FERM BP-5643, respectively (see International Patent Application WO 98/14580).

For chimeric antibody or humanized antibody, the C region of human antibody is used, and as the C region of human antibody that exhibits cytotoxic activity, human Cγ, for example Cγ1, Cγ2, Cγ3, and Cγ4 can be used. Among them, antibody having Cγ1 and Cγ3 in particular has potent cytotoxic activity, i.e. ADCC activity and CDC activity, and is preferably used in the present invention.

Chimeric antibody consists of the variable region of antibody derived from a mammal other than the human and the C region derived from human antibody, whereas humanized antibody consists of the complementarity determining region of antibody derived from a mammal other than the human and the framework region (FR) and the C region of antibody derived from human antibody. Accordingly, antigenicity thereof in the human body has been reduced so that they are useful as the active ingredient of the therapeutic agents of the present invention.

A preferred embodiment of the humanized antibody for use in the present invention includes humanized anti-HM1.24 antibody (see WO 98/14580).

In accordance with the present invention, antibodies in which sugar chains have been altered can also be used (Patent application No. 2003-207165).

In accordance with the antibody of the present invention, an anti-HM1.24 antibody having a sugar chain that contains no α-1,6 core fucose (position 6 of N-acetylglucosamine at the reducing terminal and position 1 of fucose are α-bonded), and an antibody having a sugar chain that has a bisecting N-acetylglucosamine (GlcNAc) structure have a high ADCC activity, and that an anti-HM1.24 antibody having both a sugar chain that contains no α-1,6 core fucose and a sugar chain that has a bisecting N-acetylglucosamine (GlcNAc) structure has a further higher ADCC activity.

Thus, as an antibody for use in the present invention, there can be used an antibody (anti-HM1.24 antibody) against HM1.24 antigen wherein ADCC activity has been enhanced by altering a sugar chain of said antibody. The antibody is typically a monoclonal antibody or an antibody derived therefrom, such as a chimeric antibody or, more preferably, a humanized antibody. More specifically, in accordance with the present invention, there can be used an antibody having a sugar chain that contains no α-1,6 core fucose, an antibody having a sugar chain that has a bisecting N-acetylglucosamine (GlcNAc) structure, and furthermore an antibody having both a sugar chain that contains no α-1,6 core fucose and a sugar chain that has a bisecting N-acetylglucosamine (GlcNAc) structure.

The above sugar chain-altered antibody may be produced by a method which comprises culturing YB2/0 cells having introduced therein a nucleic acid encoding an antibody (anti-HM1.24 antibody) against HM1.24 antigen, and harvesting said antibody from said culture; a method which comprises culturing a host cell having introduced therein a nucleic acid encoding N-acetylglucosaminyl transferase III (GnTIII), and harvesting said antibody from said culture; and a method which comprises culturing YB2/0 cells having introduced therein a nucleic acid encoding N-acetylglucosaminyl transferase III (GnTIII), and harvesting said antibody from said culture, and other methods.

In order to obtain anti-HM1.24 antibody of the present invention in which the ADCC activity has been enhanced by the modification of sugar chains, it is necessary to express anti-HM1.24 antibody in a host cell having no or little ability to impart α-1,6 core fucose or to express anti-HM1.24 antibody in a host cell having an ability of forming a bisecting N-acetylglucosamine (GlcNAc) structure on a sugar chain. To that end, a gene encoding the desired anti-HM1.24 antibody must be cloned. Anti-HM1.24 antibodies encoded by the cloned gene include, for example, monoclonal antibodies, chimeric antibodies in which the variable region is derived from an animal other than the human and the constant region is derived from a human antibody, humanized antibodies in which the complementarity determining region alone of the variable region is derived from an antibody of an animal other than the human and the other regions of the antibody are derived from a human antibody, and the like.

As can be seen from the description in WO 98/14580, the hybridoma that produces the monoclonal anti-HM1.24 antibody has already been established and has been deposited on Apr. 27, 1995 with the Patent Microorganism Depositary of the National Institute of Industrial Science and Technology (Chuo Dai 6, 1-1, Higashi 1-chome, Tsukuba city, Ibaraki Pref., Japan) as FERM BP-5233. From this hybridoma, DNA encoding a light chain variable region (L chain V region) and DNA encoding a heavy chain variable region (H chain V region) have been cloned, and *E. coli* having the plasmids containing these DNA's have been deposited on Aug. 29, 1996 with the Patent Microorganism Depositary of the National Institute of Industrial Science and Technology (Chuo Dai 6, 1-1, Higashi 1-chome, Tsukuba city, Ibaraki Pref., Japan) as *Escherichia coli* DH5α (pUC19-1.24L-gκ) (FERM BP-5646) and *Escherichia coli* DH5α (pUC19-1.24H-gγ1) (FERM BP-5644), respectively.

Furthermore, from the above cloned DNA encoding the L chain V region and DNA encoding the H chain V region, chimeric anti-HM1.24 antibody and humanized anti-HM1.24 antibody were created. For the humanized antibody, as shown in Table 1 to Table 4 on pages 37-40 in WO 98/14580, versions a and b were created for the L chain of the humanized antibody, and versions a to s were created for the H chain, and from the measurement of antigen-binding activity of humanized antibodies created by combining them, it was confirmed that humanized antibodies comprising the combination of the L chain version a and the H chain version r or s produce a potent antigen-binding activity.

Thus, in accordance with the present invention, various monoclonal antibodies, chimeric antibodies, humanized antibodies etc. described in WO 98/14580 cited above can be used. In addition to the above antibodies, however, there can be used chimeric antibodies, humanized antibodies etc. derived from other monoclonal antibodies against HM1.24. As methods of preparation in such cases, there can be used one described in, for example, WO 98/14580.

Figure 9:
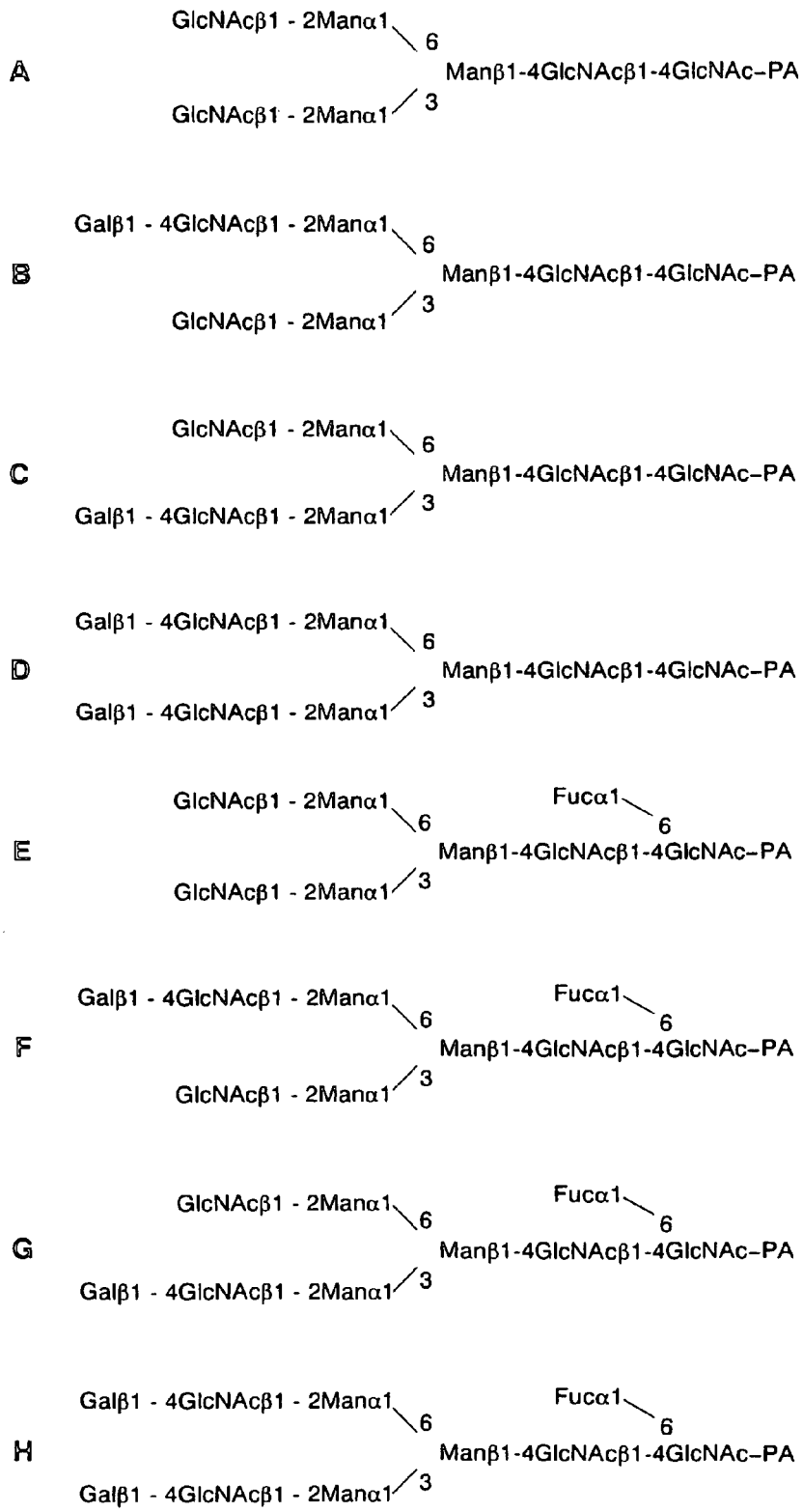
FIG. 9 shows the structures of sugars A-H as shown in FIG. 8 and Table 1.

Sugar chains that bind to anti-HM1.24 antibody include N-glycoside-linked sugar chains that bind to the side chain N atom of asparagine of the antibody molecule, and O-glycosyl-linked sugar chains that bind to the side chain hydroxyl group of serine or threonine of the antibody molecule, and the side chains of which presence or absence concerns in the present invention are the N-glycoside-linked sugar chains. The N-glycosyl-linked sugar chains, as shown in FIGS. 9 and 10, have a basic structure (core) [-Manβ1-4GlcNAcβ1-4GlcNc-] in which one mannose (Man) and two N-acetylglucosamines (GlcNAc) are bound via the β1,4-linkage, and GlNAc on the right of the structure is referred to as the reducing terminal and Man on the left is referred to as the non-reducing terminal. When fucose (Fuc) is bound, N-acetylglucosamine on the position 6 of the reducing terminal and the position 1 of fucose are mainly α-linked.

According to one aspect of the present invention, anti-HM1.24 antibody has a sugar chain that does not contain the above fucose. When an antibody molecule has a plurality of N-glycosyl sugar chains, at least one sugar chain does not have the above fucose. Such an antibody having a fucose-free sugar chain may be produced by expressing said antibody in a cell deficient of an ability of adding fucose to the sugar chain or a host that has no or low fucose-transferring ability.

In accordance with the present invention, any hosts that have no or low fucose-transferring ability can be used, and as a specific example, there can be mentioned the rat myeloma YB2/3HL.P2.G11.16Ag.20 cells (abbreviated as the YB2/0 cells) (stored as ATCC CRL 1662). Other cells that can be used in this invention include, for example, the FTVIII knockout CHO cell (WO 02/31140), and the Lec13 cell (WO 03/035835), the fucose transporter-deficient cell (Japanese Patent application No. 2003-174006, Japanese Patent application No. 2003-282081, Japanese Patent application No. 2003-174010, Japanese Patent application No. 2003-282102).

According to another aspect of the present invention, the anti-HM1.24 antibody of the present invention has a sugar chain that has bisecting N-acetylglucosamine. N-glycosyl-linked sugar chains have the basic structure (core) as described above, and on the non-reducing terminal thereof, as shown in FIG. 9, two chains containing mannose are bound via a α1,6-linkage and a α1,3-linkage. On the other hand, in the sugar chain shown in FIG. 10, one N-acetylglucosamine (GlcNAc) is bound via a β1,4-linkage in addition to the above two sugar chains on the non-reducing terminal of the basic structure (core). This N-acetylglucosamine (GlcNAc) is the "bisecting N-acetylglucosamine."

Sugar chains having bisecting N-acetylglucosamine are O-glycosyl-linked sugar chains or N-glycosyl-linked sugar chains, and are formed by transferring N-acetylglucosamine to sugar chains with N-acetylglucosaminyl transferase III (GnTIII). A gene encoding this enzyme has already been cloned, and the amino acid sequence and the nucleotide sequence of DNA encoding it have been described (NCBI database (ACCESSION D13789)). This DNA can also be cloned according to a standard method such as the PCR method based on the above sequence information.

In order to form sugar chains that have bisecting N-acetylglucosamine using DNA encoding GnTIII, a host cell that produces anti-HM1.24 antibody may be transformed with an expression vector comprising this DNA. Thus, an expression vector comprising DNA encoding GnTIII and an expression vector comprising DNA encoding anti-HM1.24 antibody are used to transform a host cell, which is then cultured.

According to the third aspect of the present invention, the anti-HM1.24 antibody of the present invention has both a sugar chain that does not have α-1,6 core fucose and a sugar chain that has bisecting N-acetylglucosamine. In order to produce this type of antibody, an expression vector comprising DNA encoding GnTIII and an expression vector comprising DNA encoding anti-HM1.24 antibody are used to transform a host cell, such as the YB2/0 cell, that has no or little activity for forming a sugar chain having α-1,6 core fucose, and then the cell is cultured.

Transformation of host cells, culturing, and isolation and purification of antibody from the culture may be carried out according to standard methods.

Antibody Fragments

As used herein, part of a full-length antibody or antibody fragment may be artificially prepared to replace partially or completely the effect of antibody.

Antibody fragments generally refer to antigen-binding regions or variable regions. For example, antibody fragments comprise Fab, Fab', F(ab')$_2$ and Fv fragments. The papain digestion of antibody produces two identical antigen-binding fragments, called Fab fragments, each having one antigen-binding site, and the remaining fragment which is called Fc because of its easily crystalizable nature. Also, its digestion with pepsin produces a F(ab')$_2$ fragment that has two antigen-binding sites and that can crosslink antigens, and the remaining different fragment (called pFc'). Other fragments include diabody (diabodies), linear antibodies, single stranded antibody molecules, and multi-specific antibodies created from antibody fragments.

The Fv fragment is the smallest antibody fragment, and contains a complete antigen-recognition site and a binding site. This region is a dimer ($V_H$-$V_L$ dimer) in which one variable domain of the heavy chain and one variable domain of the L chain are tightly bound by a non-covalent bond. Three CDRs of each variable domain interact with one another thereby to create an antigen-binding site on the surface of the $V_H$-$V_L$ dimer. The six CDRs impart antigen-binding sites to the antibody. However, even one variable domain (or, a half of an Fv containing only three CDRs that are specific for antigen) of which affinity is lower than the total binding sites has an ability of recognizing and binding to the antigen.

Furthermore, a Fab fragment (also called F(ab)) comprises light chain constant domains and a heavy chain constant domain (CH1). A Fab' fragment differs from the Fab fragment in that the former additively has several residues derived from the carboxy terminal of the heavy chain CH1 domain, said residues comprising one or more than one cysteine derived from the hinge region of the antibody.

As used herein, a diabody (diabodies) refers to a small antibody fragment having two antigen-binding sites, and the fragment contains a heavy chain variable domain (VH) linked to the light chain variable domain (VL) (VH-VL) in the same polypeptide chain. When a short linker (too short to enable the binding of two domains) is used in the same chain, the two domains pair with the constant domain of the other chain, thus creating two antigen-binding sites. A more detailed description of a diabody may be found in, for example, EP404,097, WO 93/11161, and Holliner et al. (Proc. Natl. Acad. Sci. USA (1993) 90, 6444).

A single stranded antibody (hereinafter referred to as single stranded Fv or sFv) or a sFV antibody fragment contains a VH and VL domain of antibody, and these domains are present in a single polypeptide chain. Generally, a Fv polypeptide further comprises a polypeptide linker in between the VH and the VL domain, by means of which a structure necessary for antigen binding can be formed. sFv is described in Pluckthun "The Pharmacology of Monoclonal Antibodies" Vol. 113 (Rosenburg and Moore ed., Springer Verlag, New York, pp. 269-315 (1994)).

Antibody Phage Library

In accordance with the present invention, an antibody phage library can be used in order to obtain DNA encoding the monoclonal antibody of interest.

In order to isolate antibody or antibody fragments from an antibody phage library, an antibody phage library produced using a technology described in, for example, McCafferty et al. (Nature (1990), 348, 552) may be used. The isolation of mouse and human antibody using a phage library may be carried out using a method described by Clackson et al. (Nature (1991) 352, 624) and Marks et al. (J. Mol. Biol. (1991) 222, 581).

Also a method based on chain shuffling (Marks et al., Bio/Technology (1992) 10, 779) may be used to obtain a high affinity (an order of about nM) human antibody. As a method to construct a huge phage library, combinatorial infection and in vivo recombination (Waterhouse et al., Nucleic Acids Res.

21:2265-2266 (1993)) are known. These technologies can also replace the conventional monoclonal antibody-hybridoma technology.

Human Antibody-Producing Transgenic Animals

In accordance with the present invention, a hybridoma that produces human antibody can be directly obtained using a human antibody-producing transgenic animal.

A human antibody can be obtained by immunizing a human antibody-producing transgenic mammal with an immunogen (antigen) and then harvesting the antibody using a common existing method for antibody production. The antibody gene may be cloned from the cells and then integrated into an suitable vector, which is then introduced into a host to produce a recombinant antibody using gene recombinant technology.

The method of preparing a human antibody-producing non-human transgenic mammal to be used, specifically a human antibody-producing transgenic mouse, is known (Nature Genetics (1994) 7, 13: Nature Genetics (1997) 15, 146; Kohyo (National Publication of Translated Version) No. 4-504365; Kohyo (National Publication of Translated Version) No. 7-509137; Nikkei Science (1995) 6, 40; International Patent Publication WO 94/25585; Nature (1994) 368, 856; Kohyo (National Publication of Translated Version) No. 6-500233, etc.). The above human antibody-producing non-human transgenic mammal may specifically prepared in a method as follows:

(1) a step of creating a knock-out non-human mammal in which an immunoglobulin heavy chain gene inherent in said non-human mammal has been functionally inactivated by replacing at least part of the immunoglobulin heavy chain gene locus inherent in said animal with a drug resistance marker gene (such as neomycin resistant gene etc.) by homologous recombination;

(2) a step of creating a knock-out non-human mammal in which an immunoglobulin light chain gene (specifically κ chain gene etc.) inherent in said non-human mammal has been functionally inactivated by replacing at least part of the immunoglobulin light chain gene locus inherent in said animal with a drug resistance marker gene (such as neomycin resistant gene etc.) by homologous recombination;

(3) a step of creating a transgenic non-human mammal in which the desired region of a human immunoglobulin heavy chain gene locus has been integrated into a mouse chromosome using a vector capable of transporting a large gene as represented by the yeast artificial chromosome (YAC) vector etc.;

(4) a step of creating a transgenic non-human mammal in which the desired region of a human immunoglobulin light chain gene (specifically κ chain gene) locus has been integrated into a mouse chromosome using a vector capable of transporting a large gene as represented by the YAC etc.; and (5) a step of creating a transgenic non-human mammal in which both of an immunoglobulin heavy chain gene locus inherent in said non-human mammal and an immunoglobulin light chain gene locus inherent in said non-human mammal have been functionally inactivated and both of the desired region of a human immunoglobulin heavy chain gene locus and the desired region of a human immunoglobulin light chain gene locus have been integrated into the chromosome of said non-human mammal by crossing the non-human mammal and the transgenic non-human mammal of the above (1)-(4) in any order.

As described above, the immunoglobulin gene locus inherent in a non-human mammal can be inactivated so as not to be reconstituted by replacing a suitable region of said gene locus with a foreign marker gene (such as neomycin resistant gene etc.) by homologous recombination. For inactivation using said homologous recombination, a method, for example, called the positive negative selection (PNS), may be used (Nikkei Science (1994) 5, 52). Also, the functional inactivation of a immunoglobulin heavy chain gene locus can be accomplished by introducing, for example, impairment in part of the J region or the C region (such as Cμ region), and the functional inactivation of a immunoglobulin light chain (such as κ chain) can be accomplished by introducing, for example, impairment in part of the J region or the C region, or in a region spanning the J region and the C region.

Transgenic animals can be produced by a conventional method (see for example SAISHIN DOBUTSU SAIBO JIKKENN MANYUARU (The Latest Manual on Experiment for Animal Cells), issued by LIC, Chapter 7, pp. 361-408 (1990)). Specifically, the hypoxanthine phosphoribosyltransferase (HRPT)-negative embryonic stem (ES) cell derived from a normal non-human animal blastocyst is fused by spheroplast fusion with a yeast containing a YAC vector in which the gene encoding said human immunoglobulin heavy chain gene locus or light chain gene locus or a part thereof and the HRPT gene have been inserted.

ES cells in which said foreign gene has been integrated on the gene inherent in the mouse are selected by HAT selection. Then, the ES cells selected are microinjected into a fertilized ovum (blastocyst) harvested from another normal non-human mammal (Proc. Natl. Acad. Sci. USA (1980) 77, 7380; U.S. Pat. No. 4,873,191). The implantation of said blastocyst into the womb of another non-human mammal which is to be a surrogate mother gives rise to a chimeric transgenic non-human mammal. Said chimeric animal is crossed with a normal non-human mammal to create a heterotransgenic non-human mammal. By crossing said heterotransgenic mammals with each other, homotransgenic non-human mammals can be obtained based on the Mendel's law.

Expression and Production

Antibody genes constructed as described above may be expressed and obtained in a known method. In the case of mammalian cells, expression may be accomplished using an expression vector containing a commonly used useful promoter, the antibody gene to be expressed, and DNA in which the poly A signal has been operably linked at 3' downstream thereof or a vector containing said DNA. Examples of the promoter/enhancer include human cytomegalovirus immediate early promoter/enhancer.

Additionally, as the promoter/enhancer which can be used for the expression of antibody for use in the present invention, there can be used viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Nature (1979) 277, 108) when SV40 promoter/enhancer is used, or by the method of Mizushima et al. (Nucleic Acids Res. (1990) 18, 5322) when HEF1α promoter/enhancer is used.

In the case of E. coli, expression may be conducted by operably linking a commonly used useful promoter, a signal sequence for antibody secretion, and the antibody gene to be expressed, followed by expression thereof. As the promoter, for example, there can be mentioned lacZ promoter and araB promoter. The method of Ward et al. (Nature (1098) 341, 544-546; FASEB J. (1992) 6, 2422-2427) may be used when lacZ promoter is used, and the method of Better et al. (Science (1988) 240, 1041-1043) may be used when araB promoter is used.

As the signal sequence for antibody secretion, when produced in the periplasm of *E. coli*, the pelB signal sequence (Lei, S. P. et al., J. Bacteriol. (1987) 169, 4379) can be used. After separating the antibody produced in the periplasm, the structure of the antibody is appropriately refolded before use (see, for example, WO 96/30394).

As the origin of replication, there can be used those derived from SV40, polyoma virus, adenovirus, bovine papilloma virus (BPV) and the like. Furthermore, for the amplification of the gene copy number in the host cell system, expression vectors can include as selectable markers the aminoglycoside transferase (APH) gene, the thymidine kinase (TK) gene, *E. coli* xanthine guaninephosphoribosyl transferase (Ecogpt) gene, the dihydrofolate reductase (dhfr) gene and the like.

For the production of antibody for use in the present invention, any production system can be used. The production system of antibody preparation comprises the in vitro and the in vivo production system. As the in vitro production system, there can be mentioned a production system which employs eukaryotic cells and the production system which employs prokaryotic cells.

When the eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as *Xenopus oocytes*, or (3) insect cells such as sf9, sf21, and Tn5. Known plant cells include, for example, those derived from the genus *Nicotiana*, more specifically cells derived from *Nicotiana tabacum*, which is subjected to callus culture. Known fungal cells include yeasts such as the genus *Saccharomyces*, more specifically *Saccharomyces cereviseae*, or filamentous fungi such as the genus *Aspergillus*, more specifically *Aspergillus niger*.

When the prokaryotic cells are used, there are the production systems which employ bacterial cells. Known bacterial cells include *Escherichia coli* (*E. coli*), and *Bacillus subtilis*.

By introducing via transformation the gene of the desired antibody into these cells and culturing the transformed cells in vitro, the antibody can be obtained. Culturing is conducted in the known methods. For example, as the culture liquid, DMEM, MEM, RPMI1640, and IMDM can be used, and serum supplements such as fetal calf serum (FCS) may be used in combination. In addition, antibodies may be produced in vivo by implanting cells into which the antibody gene has been introduced into the abdominal cavity of an animal, and the like.

As further in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). Also, as insects, silkworms can be used.

When plants are used, tobacco, for example, can be used. Antibody genes are introduced into these animals or plants, and the antibodies are produced in such animals or plants, and recovered therefrom. For example, an antibody gene is inserted into the middle of the gene encoding protein which is inherently produced in the milk such as goat β casein to prepare fusion genes. DNA fragments containing the fusion gene into which the antibody gene has been inserted are injected into a goat embryo, and the embryo is introduced into a female goat. The desired antibody is obtained from the milk produced by the transgenic goat borne to the goat who received the embryo or offsprings thereof. In order to increase the amount of milk containing the desired antibody produced by the transgenic goat, hormones may be given to the transgenic goat as appropriate. (Ebert, K. M. et al., Bio/Technology (1994) 12, 699-702).

When silkworms are used, baculovirus into which the desired antibody gene has been inserted is infected to the silkworm, and the desired antibody can be obtained from the body fluid of the silkworm (Susumu, M. et al., Nature (1985) 315, 592-594). Moreover, when tobacco is used, the desired antibody gene is inserted into an expression vector for plants, for example pMON 530, and then the vector is introduced into a bacterium such as *Agrobacterium tumefaciens*. The bacterium is then infected to tobacco such as *Nicotiana tabacum* to obtain the desired antibody from the leaves of the tobacco (Julian, K.-C. Ma et al., Eur. J. Immunol. (1994) 24, 131-138).

When antibody is produced in the in vitro or in vivo production systems, as described above, DNA encoding the heavy chain (H chain) or the light chain (L chain) of antibody may be separately integrated into an expression vector and the hosts are transformed simultaneously, or DNA encoding the H chain and the L chain may be integrated into a single expression vector and the host is transformed therewith (see International Patent Application WO 94-11523).

The antibody produced as described above can be bound to various molecules such as polyethylene glycol (PEG) for use as a modified antibody. "Antibody" as used herein includes these modified antibodies. In order to obtain these modified antibody, the antibody obtained may be chemically modified. These methods have already been established in the field of the art.

Separation and Purification of Antibody

Antibodies produced and expressed as described above can be separated from the inside or outside of the cell or from the host and then may be purified to homogeneity. Separation and purification of the antibody for use in the present invention may be accomplished by affinity chromatography. As the column used for such affinity chromatography, there can be mentioned Protein A column and Protein G column. Examples of the carrier for use in Protein A column are Hyper D, POROS, Sepharose F.F. and the like.

Alternatively, methods for separation and purification conventionally used for proteins can be used without any limitation. Separation and purification of the antibody for use in the present invention may be accomplished by combining, as appropriate, chromatography other than the above-mentioned affinity chromatography, filtration, ultrafiltration, salting-out, dialysis and the like. Chromatography includes, for example, ion exchange chromatography, hydrophobic chromatography, gel-filtration and the like.

Conjugates with a Drug or a Toxin

In accordance with the present invention, antibodies may be conjugated to various reagents and used for therapeutic purposes. Such reagents include, for example, chemotherapeutic agents such as doxorubicin, methotrexate and taxol, heavy metals, radionuclides such as Iodine-131 and Yttrium-90, and toxins such as Pseudomonas toxin. For a method of producing conjugates with therapeutic reagents and of using them for therapeutic purposes, see U.S. Pat. No. 5,057,313 and No. 5,156,840.

Determination of Antibody Concentration

The concentration of antibody obtained in the above method can be determined by the measurement of absorbance or by ELISA and the like. Thus, when absorbance measurement is employed, the antibody for use in the present invention or a sample containing the antibody is appropriately diluted with PBS(−) and then the absorbance is measured at 280 nm, followed by calculation using the absorption coefficient of 1.35 OD at 1 mg/ml. When the ELISA method is used, measurement is conducted as follows. 100 μl of goat anti-human IgG (manufactured by BIO SOURCE) diluted to 1 μg/ml in 0.1 M bicarbonate buffer, pH 9.6, is added to a 96-well plate (manufactured by Nunc), and is incubated overnight at 4° C. to immobilize the antibody. After blocking, 100 μl each of appropriately diluted antibody of the present invention or a sample containing the antibody, or 100 μl of human IgG (manufactured by CAPPEL) as the standard is added, and incubated at room temperature for 1 hour. After washing, 100 μl of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550 (manufactured by Bio-Rad) to calculate the concentration of the desired antibody.

FCM Analysis

Reactivity of the antibody of the present invention with myeloma cells may be examined by flow cytometry (FCM) analysis. As the cells, established cell lines or freshly isolated cells can be used. As established cell lines, there may be used human breast cancer cell lines MCF7 (ATCC HTB-22) and MDA-MB-231 (ATCC HTB-26), human colon cancer cell lines COLO 205 (ATCC CCL-222) and WiDr (ATCC CCL-218), a human pancreatic cancer cell line BxPC-3 (ATCC CRL-1687), a human cervical cancer cell line UCC-5 (The Central Institute for Experimental Animals), a human kidney cancer cell line Caki-1 (ATCC HTB-46), a human ovarian cancer cell line PA-1 (ATCC CRL-1572) and the like may be used.

After washing the above cells in PBS(−), 100 μl of antibody or a control antibody diluted to 25 μg/ml in the FACS buffer (PBS(−) containing 2% bovine fetal serum and 0.05% sodium azide) is added thereto, which is then incubated on ice for 30 minutes. After washing with the FACS buffer, 100 μl of 25 μg/ml FITC-labeled goat anti-mouse antibody (GAM, manufactured by Becton Dickinson) is added thereto, and the antibody is then incubated on ice for 30 minutes. After washing with the FACS buffer, the cells are suspended in 600 μl or 1 ml of the FACS buffer, and each cell may be measured for its fluorescence intensity using the FACScan (manufactured by Becton Dickinson).

Furthermore, instead of the above indirect staining method, the cells may be treated with a high concentration of immunoglobulin, and after blocking the Fc receptor, the direct staining method using a FITC-labelled anti-HM1.24 antibody may be used for FCM analysis.

Cytotoxic Activity

Measurement of ADCC Activity

The antibody for use in the present invention is one which has, for example, an ADCC activity as the cytotoxic activity.

According to the present invention, the ADCC activity on tumor cells can be measured in the following manner. First, mononuclear cells are isolated as the effector cells (E) from human peripheral blood or bone marrow by the gravity centrifuge method.

As the target cells (Target cell: T), human breast cancer cell lines MCF7 (ATCC HTB-22) and MDA-MB-231 (ATCC HTB-26), human colon cancer cell lines COLO 205 (ATCC CCL-222) and WiDr (ATCC CCL-218), a human cervical cancer cell line UCC-5 (The Central Institute for Experimental Animals), and a human ovarian cancer cell line PA-1 (ATCC CRL-1572), cells derived from patients or the like is labeled with $^{51}Cr$ to be prepared as the target cells. Subsequently, to the labeled target cells is added the antibody to be measured for the ADCC activity and incubated. Effector cells at a suitable ratio to the target cells are then added and incubated.

After incubation, the supernatant is removed and measured for radioactivity using a gamma counter, whereupon 1% NP-40 can be used for measurement of the maximum free radioactivity. The cytotoxic activity (%) can be calculated as $(A-C)/(B-C) \times 100$, in which A is radioactivity (cpm) released in the presence of the antibody, B is radioactivity (cpm) released by NP-40, and C is radioactivity (cpm) released by the medium alone containing no antibody.

Enhancement of Cytotoxic Activity

In order to exhibit cytotoxic activity such as an ADCC activity, it is preferred to use Cγ, in particular Cγ1 and Cγ3 as the constant region (C region) of antibody in humans. Furthermore, a more potent ADCC activity or CDC activity can be induced by adding, altering, or modifying part of the amino acids in the C region of antibody.

By way of example, there can be mentioned the construction of an IgM-like polymer of IgG by amino acid substitution (Smith, R. I. F. & Morrison, S. L. BIO/TECHNOLOGY (1994) 12, 683-688), the construction of an IgM-like polymer of IgG by amino acid addition (Smith, R. I. F. et al., J. Immunology (1995) 154, 2226-2236), the expression of a tandemly-ligated gene encoding L chain (Shuford, W. et al., Science (1991) 252, 724-727), the dimerization of IgG by amino acid substitution (Caron, P. C. et al., J. Exp. Med. (1992) 176, 1191-1195, Shopes, B., J. Immunology (1992) 148, 2918-2922), the dimerization of IgG by chemical modification (Wolff, E. A. et al., Cancer Res. (1993) 53, 2560-2565), and the introduction of the effector function by altering an amino acid(s) in the hinge region of antibody (Norderhaug, L. et al., Eur. J. Immunol. (1991) 21, 2379-2384) and the like.

These can be accomplished by means of the oligomer site-specific mutagenesis using a primer, the addition of a nucleotide sequence using a restriction enzyme cleavage site, and the use of a chemical modifier that creates a covalent bond.

Administration Routes and Pharmaceutical Formulations

The therapeutic agents for solid tumors of the present invention can be administered parenterally or orally, and systemically or locally. For example, intravenous injection such as drip infusion, intramuscular injection, intraperitoneal injection and subcutaneous injection can be selected, and, depending on the age and the condition of the patient, a suitable method of administration can be selected. An effective dosage may be selected in the range of 0.01-100 mg/kg body weight per administration. Alternatively, a dosage of 10-2000 mg, preferably 100-1000 mg/patient can be selected.

The therapeutic agents for solid tumors of the present invention may simultaneously contain pharmaceutically acceptable carriers and additives depending on the route of administration.

As examples of such carriers and additives, there can be mentioned water, pharmaceutically acceptable organic solvents, collagen, polyvinyl alcohol, polyvinyl pyrrolidone, carboxy vinyl polymers, sodium carboxymethyl cellulose, sodium polyacrylate, sodium alginate, water-soluble dextran, sodium carboxymethyl starch, pectin, methyl cellulose, ethyl cellulose, xanthan gum, gum Arabic, casein, gelatin, agar, diglycerin, propylene glycol, polyethylene glycol, vaseline, paraffin, stearyl alcohol, stearic acid, human serum albumin (HSA), mannitol, sorbitol, lactose, surfactants acceptable as pharmaceutical additives, and the like. Depending on the dosage form, additives to be used may be selected from, but not limited to, the above or from the combinations thereof.

The subject diseases to be treated of the present invention are solid tumors, excluding hematopoietic tumors, that have antigens to which the antibody for use in the present invention binds on the target tumor cells. Specifically, there can be mentioned head and neck cancer, small cell lung cancer, non-small cell lung cancer, esophageal cancer, breast cancer, gastric cancer, colon cancer, rectal cancer, hepatic cancer, biliary tract cancer, pancreatic cancer, ovarian cancer, cervical cancer, endometrial cancer, prostate cancer, kidney cancer, bladder cancer, skin cancer, brain tumor, pediatric solid tumor, malignant bone tumor and the like. There can also be mentioned metastasis and metastatic lesions of these solid tumors, and carcinomatous pleuritis, cancerous peritonitis and cancerous meningitis etc. associated with solid tumors. The therapeutic agents of the present invention are effective as therapeutic agents for these solid tumors excluding hematopoietic tumors.

EXAMPLES

The present invention will now be explained with reference to examples, but it should be noted that the present invention is not limited to these examples in any way.

Example 1

Reactivity of Anti-HM1.24 Antibody With Solid Tumor Cell Lines

1. Flow Cytometry Analysis

Human breast cancer cell lines MCF7 (ATCC HTB-22) and MDA-MB-231 (ATCC HTB-26), human colon cancer cell lines COLO 205 (ATCC CCL-222) and WiDr (ATCC CCL-218), a human pancreatic cancer cell line BxPC-3 (ATCC CRL-1687), a human cervical cancer cell line UCC-5 (The Central Institute for Experimental Animals), a human kidney cancer cell line Caki-1 (ATCC HTB-46) and a human ovarian cancer cell line PA-1 (ATCC CRL-1572) were used.

For these cells, after about $1 \times 10^6$ cells each were suspended in 80 µl of FACS/PBS (prepared by dissolving 1 g of bovine serum albumin (manufactured by Sigma) in 1 L of CellWASH (manufactured by Becton Dickinson)), 200 µg/ml of fluorescently labelled humanized anti-HM1.24 antibody (prepared by labelling humanized anti-HM1.24 antibody with NHS-fluorescein (manufactured by PIERCE)) or fluorescently labelled human IgG1 (prepared by labelling human IgG1 (manufactured by Sigma) with NHS-fluorescein) or 20 µl of FACS/PBS were added, and were allowed to react on ice for 30 minutes. After washing twice with 1 ml of FACS/PBS, they were suspended in 1 ml of FACS/PBS, and the fluorescence intensity of the cells was measured using a flow cytometer (EPICS XL, manufactured by BECKMAN COULTER).

2. Result

Anti-HM1.24 antibody exhibited reactivity with all cell lines tested (FIG. 1, FIG. 2 and FIG. 3).

Example 2

ADCC Activity by Anti-HM1.24 Antibody to Solid Tumor Cell Lines

The determination of ADCC activity was carried out according to a method in Current Protocols in Immunology, Chapter 7, Immunologic studies in humans, Editor, John E., Coligan et al., John Wiley & Sons, Inc., 1993.

1. Preparation of Target Cells

Human breast cancer cell lines MCF7 (ATCC HTB-22) and MDA-MB-231 (ATCC HTB-26), human colon cancer cell lines COLO 205 (ATCC CCL-222) and WiDr (ATCC CCL-218), a human cervical cancer cell line UCC-5 (The Central Institute for Experimental Animals) and a human ovarian cancer cell line PA-1 (ATCC CRL-1572) were used as the target cells.

Each cell was plated on a 96-well flat-bottomed plate (manufactured by Becton Dickinson) at $3 \times 10^3$/well ($2 \times 10^3$/well for COLO 205, Widr, and $5 \times 10^3$/well for UCC5, and $1 \times 10^3$/well for PA-1) and incubated for three days. After incubation, $^{51}$Cr-sodium chromate (manufactured by Amersham Pharmacia Biotech) was added to a final concentration of 50 µCi/ml, which was incubated at 37° C. for one hour for radiolabelling. After labelling, the cells were washed in a RPMI 1640 medium (manufactured by GIBCO) containing 10% fetal bovine serum (FBS, manufactured by HyClone), to which 50 µl of the same medium was added to prepare the target cell.

2. Preparation of Effector Cells

From the peripheral blood of normal healthy adult volunteers, mononuclear cells were isolated using Ficoll-Paque™ PLUS (manufactured by Amersham Pharmacia Biotech). The cell concentration was adjusted to $1 \times 10^7$/ml with a RPMI 1640 medium containing 10% FBS to prepare the effector cell.

3. Determination of ADCC Activity

Humanized anti-HM1.24 antibody or human IgG1 was diluted with a RPMI 1640 medium containing 10% FBS, and 50 µl thereof was added to the target cell, and incubated on ice for 15 minutes. Then 100 µl of effector cells was added, and cultured in a carbon dioxide gas incubator at 37° C. for four hours. The final concentration of antibody was 0 or 10 µg/mL. After incubation, 100 µl of the supernatant was collected, and the radioactivity thereof was determined using a gamma counter (COBRAIIAUTO-GAMMA, MODEL D5005, manufactured by Packard Instrument Company). The cytotoxic activity by ADCC was determined from the following calculation formula. The maximum radioactivity released was determined by adding 1% NP-40 (manufactured by Nacalai Tesque Inc.). The cytotoxic activity was determined after destructing cells by adding 1% NP-40 to the target cell. The cytotoxic activity (%) was determined from (A–C)/(B–C)/100. As used herein, A represents radioactivity (cpm) released in the presence of antibody and B represents radioactivity (cpm) released with NP-40, and C represents radioactivity (cpm) released with the culture medium alone.

4. Results

Humanized anti-HM1.24 antibody exhibited AD activity against MCF7, MDA-MB231, COLO 205, WiDr, UCC-5, and PA-1 (FIG. 4).

Reference Example 1

Expression of Humanized Anti-Human HM1.24 Antibody in Rat Myeloma YB2/0

Ten µg of a vector expressing humanized anti-human HM1.24 antibody (AHi/N5KG1V-lark, Barnett, R. S. et al., Antibody Production in Chinese Hamster Ovary Cells Using an Impaired Selectable Marker. In: Wang, H. Y. & Imanaka, T. (eds) ACS Symposium Series Voal 604: Antibody Expression and Engineering, 27, 1995, WO 98/4580) was introduced into $2 \times 10^6$/0.6 ml PBS(–) of YB2/0 (ATCC CRT-1662) by electroporation at a condition of 1.5 kV and 25 µF. Culturing was carried out in a 5% CO2 incubator at 37° C.

After 400 µg/ml of Geneticin was added to the RPMI 1640 medium (Gibco) containing 10% FCS for selection, the gene was amplified at sequentially increasing concentrations of 50 nM MTX, 100 nM MTX, and 200 nM MTX. Also 0.5 cells/100 µL/well was plated into a 10% FCS/RPMI 1640 containing 200 nM MTX and 400 µg/ml of Geneticin in a 96-well plate (Falcon) in order to clone cells by the limiting dilution method.

The culture supernatant of the YB2/0 cells into which the gene of humanized anti-human HM1.24 antibody had been introduced was determined by ELISA shown in Reference Example 2.

Reference Example 2

Determination of Humanized Anti-HM1.24 Antibody (ELISA Method)

To a 96-well ELISA plate (manufactured by Nunc), soluble HM1.24 antigen diluted to about 100 ng/ml with a coat buffer (100 mmol/L sodium hydrogen carbonate, pH 9.6) was added in portions of 100 µL, and then incubated at 4° C. overnight or longer. After incubation, 1% BSA-PBS was added at 200 µL/well and then allowed to stand at room temperature for about two hours, and the prepared plate was stored at 4° C. After 1% BSA-PBS was decanted off, each well was washed with Tween-PBS.

Appropriately diluted humanized anti-HM1.24 antibody standard solutions or sample solutions and biotin-labelled humanized anti-HM1.24 antibody diluted to 100 ng/ml were mixed at 1:1, and then aliquoted at 100 µL/well. After incubating for 1 hour at room temperature, each well was washed with Tween-PBS. Avidin-labelled HRP was added to each well, incubated at room temperature for 15 minutes or longer, TMB liquid (manufactured by Sigma) was added thereto at 100 µL/well, and 50 µL/well of 2 mol/L sulfuric acid was added to stop the reaction, and then absorbance at 450 nm was measured. From the calibration curve of concentration-absorbance for humanized anti-HM1.24 antibody standard solutions, the humanized HM1.24 antibody concentration of the sample solutions was calculated.

Reference Example 3

Purification of Humanized Anti-Human M1.24 Antibody Expressed in YB2/0

Cells for which the expression of humanized anti-human HM1.24 antibody was confirmed were subjected to an expansion culture in a 1700 cm$^2$ roller bottle (CORNING). Thus, 1×10$^9$ humanized anti-human HM1.24 antibody-expressing YB2/0 cells were cultured to confluence in a 400 ml of 10% FCS/RPMI 1640 medium containing 200 nM MTX and 400 µg/ml of gentamycin (2.5 rpm). Then, FCS was passed through rProtein A FF (Amersham Pharmacia) equalized with PBS(−) for collection of the culture supernatant to remove bovine-derived IgG (FCS(−)), and this FCS(−) was cultured in a 10% FCS(−)/RPMI 1640 medium containing 200 nM MTX and 400 µg/ml of gentamycin for 3-4 days.

Figure 5:
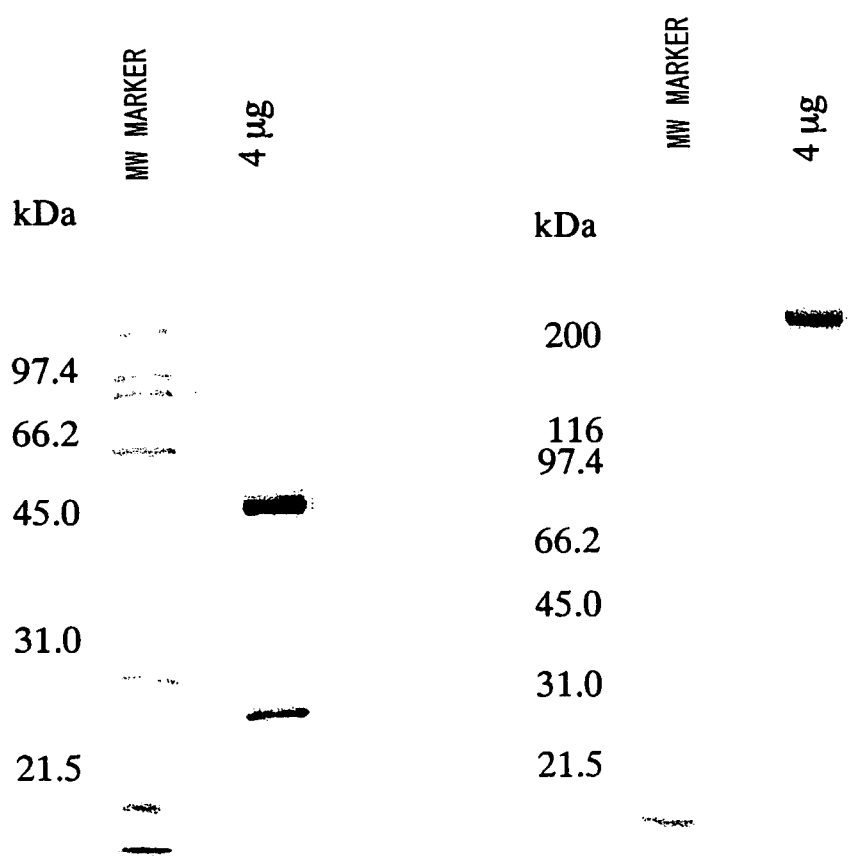
FIG. 5 shows a pattern of SDS-PAGE (12% T) of purified humanized anti-HM1.24 antibody that was expressed in YB2/0. Left: under a reducing condition, right: under a non-reducing condition. Four μg each of purified humanized anti-HM1.24 antibody was applied.

After the culture supernatant was treated with a 0.22 µm filter, it was purified with rProtein A FF (PBS/PBS-citric acid: linear gradient elution) and Source 15S (20 mM acetic acid, 0-0.5 mM NaCl: linear gradient elution). The purified humanized anti-human HM1.24 antibody was termed as HM1.24 antibody-YB (FIG. 5).

Reference Example 4

Preparation of CHO Cells Expressing HM1.24 Antigen (BST-2)

CHO cells expressing the HM1.24 antigen protein were prepared as follows (Ohtomo T. et al., Biochemical and Biophysical Research Communications 258 (1999), 583-591). Thus, an expression vector p3.19 (see supra) encoding HM1.24 antigen was introduced to a DHFR-deficient CHO cell line, 500 µg/ml of G418 was used for selection, and the limiting dilution was performed to obtain four cell lines HM26, HM31, HM21 and HM36. The number of the HM1.24 antigens expressed on the cell surface, as determined by flow cytometry in a method described in Patent application No. 2001-115889, was $3.8 \times 10^3$, $2.2 \times 10^4$, $2.2 \times 10^4$, and $1.8 \times 10^5$, respectively.

Reference Example 5

Determination of ADCC Activity Using Human Peripheral Blood-Derived PBMC (1) Preparation of Human PBMC Solution Peripheral blood drawn with heparin from a normal healthy subject was diluted two-fold with PBS(−), and layered on Ficoll-Paque™ PLUS (Amersham Pharmacia Biotech AB). After centrifuging this (500×g, 30 minutes, 20° C.), the interlayer, a mononuclear cell fraction, was collected. After washing three times, it was suspended into 10% PBS/RPMI to prepare the human PBMC solution.

(2) Preparation of the Target Cell Solution

CHO cells that express HM1.24 antigen (BST-2) described in Reference Example 4 were detached from the dish using the cell-detaching buffer (Invitrogen Corp), and were suspended in 200 µl of 10% FBS/RPMI, to which 5.55 MBq of chromium-51 was added, and incubated in a 5% carbon dioxide incubator at 37° C. for one hour. After washing the cells three times, they were prepared into an individual cell concentration in 10% FBS-RPMI 1640 medium to prepare the target cell solutions.

(3) Chromium Release Test (ADCC Activity)

After the target cell solutions were aliquoted in 50 µl portions into a 96-well U-bottomed plate, 50 µl each of antibody solutions prepared at each concentration was added thereto, and incubated on ice for one hour, then 100 µl of the human PBMC solution was added, incubated in a 5% carbon dioxide incubator at 37° C. for four hours, and then radioactivity of the 100 µl of the culture supernatant after incubation was determined by a gamma counter. The specific chromium release rate was determined based on the following formula:

Specific chromium release rate (%)=$(A-C) \times 100/(B-C)$

A represents a mean of radioactivity (cpm) for each well, B represents a mean of radioactivity (cpm) of a well in which 50 µl of a target cell suspension, 20 µl of a 10% NP-40 aqueous solution (Nonidet™ P-40, manufactured by Nacalai Tesque Inc.) and 130 µl of a 10% FBS/RPMI medium were added, and C represents a mean of radioactivity (cpm) of a well in which 50 µl of the target cell suspension and 150 µl of the 10% FBS/RPMI medium were added.

Reference Example 6

Method of Determining ADCC Activity Using a CHO Cell Line that Stably Expresses β-Galactosidase As the effector cell, mononuclear cells isolated from the peripheral blood of a normal healthy subject by the density centrifugation method was used. Thus, an equal amount of PBS was added to the peripheral blood of the normal healthy subject, layered on Ficoll-Paque PLUS (Pharmacia), and then centrifuged at 500 g for 30 minutes. The mononuclear cell phase was collected, washed three times with RPMI 1640 containing 10% FCS, and then prepared to a cell count of $5\times10^6$/ml with a α-MEM containing 10% FCS.

After detaching with trypsin-EDTA, 50 µl of the CHO#30 cell line that stably expresses β-galactosidase suspended at $2\times10^5$ cells/ml in α-MEM containing 10% FCS and 50 µl of various concentrations of anti-HM1.24 antibody were added into a 96-well U-bottomed plate, which were incubated at 4° C. for 15 minutes. Then 100 µl of the effector cells was added and incubated at 37° C. for four hours. After incubation, 20 µl of the culture supernatant was collected, and the β-galactosidase activity thereof was determined. The maximum amount of the released enzyme was set as the amount of enzyme released with a cell lysis buffer of the Galactone-star assay kit.

Cytotoxic activity was calculated as:

$$\text{Cytotoxic activity (\%)} = (A-C) \times 100/(B-C) \text{ (\% β-galactosidase)}$$

wherein, A represents the activity (RLU/sec) of β-galactosidase released in the presence of the antibody, B represents the activity (RLU/sec) of β-galactosidase released with the cell lysis buffer, and C represents the activity (RLU/sec) of β-galactosidase released with the culture liquid alone without antibody.

Reference Example 7

Figure 7:
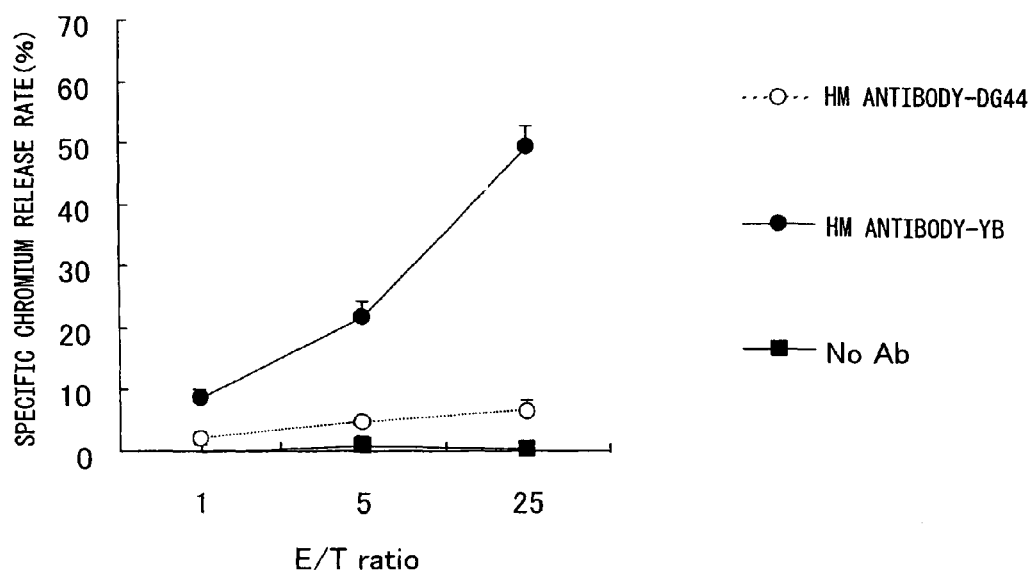
FIG. 7 is a result of ADCC activity of human PBMC at 1 μg/ml of HM1.24 antibody-DG44 and HM1.24 antibody-YB with E/T ratio=1, 5, 25 using HM31 as the target cell.

Determination of ADCC Activity of YB2/0-Derived Humanized Anti-Human HM1.24 Antibody The ADCC activity of HM1.24 antibody (HM1.24 antibody-YB) expressed in YB2/0 determined by the method described in Reference Example 5 is shown in FIG. 6 to FIG. 7. For any target cells, as shown in FIG. 6, HM1.24 antibody-YB exhibited a higher ADCC activity than the HM1.24 antibody (HM1.24 antibody-DG44) produced in DG44 (DHFR-deficient CHO cells: Urlaub, G. et al. (1986) Effect of Gamma Rays at the Dihydrofolate Reductase Locus: Deletions) and Inversions. Somatic Cell and Molecular Genetics, 12: 555, 1986).

Specifically, the induction of ADCC activity was noted at lower concentrations, and the highest ADCC activity also increased. In particular, when target cells HM26 and HM31 that express small numbers of HM1.24 antigen were used, HM1.24 antibody-DG44 exhibited very low ADCC activity whereas HM1.24 antibody-YB exhibited high ADCC activity. Also, as shown in FIG. 7 not only when the ratio (E/T ratio) of the PBMC count relative to that of the target cells was 25 but when the E/T ratio was 5, HM1.24 antibody-YB exhibited a higher ADCC activity than HM1.24 antibody-DG44.

Reference Example 8

Analysis of Sugar Chains

1. Preparation of 2-Aminopyridine-Labelled Sugar Chains (Pyridylaminated Sugar Chains)

N-Glycosidase (Roche) acted on the YB2/0-derived antibody of the present invention and the CHO-derived antibody as the control sample to release sugar chains from the protein (Weitzhandler M. et al., Journal of Pharmaceutical Sciences 83:12 (1994), 1670-1675). After the sugar chains were desalted by solid-phase extraction using a cellulose cartridge (manufactured by TAKARA) (Shimizu Y. et al., Carbohydrate Research 332 (2001), 381-388), they were concentrated to dryness, and then fluorescently labelled with 2-aminopyridine (Kondo A. et al., Agricultural and Biological Chemistry 54: 8 (1990), 2169-2170). After the pyridylaminated sugar chains obtained were desalted by solid-phase extraction using a cellulose cartridge, they were concentrated by centrifugation to prepare purified pyridylaminated sugar chains.

2. Analysis by Reverse Phase HPLC of Purified Pyridylaminated Sugar Chains

Figure 8:
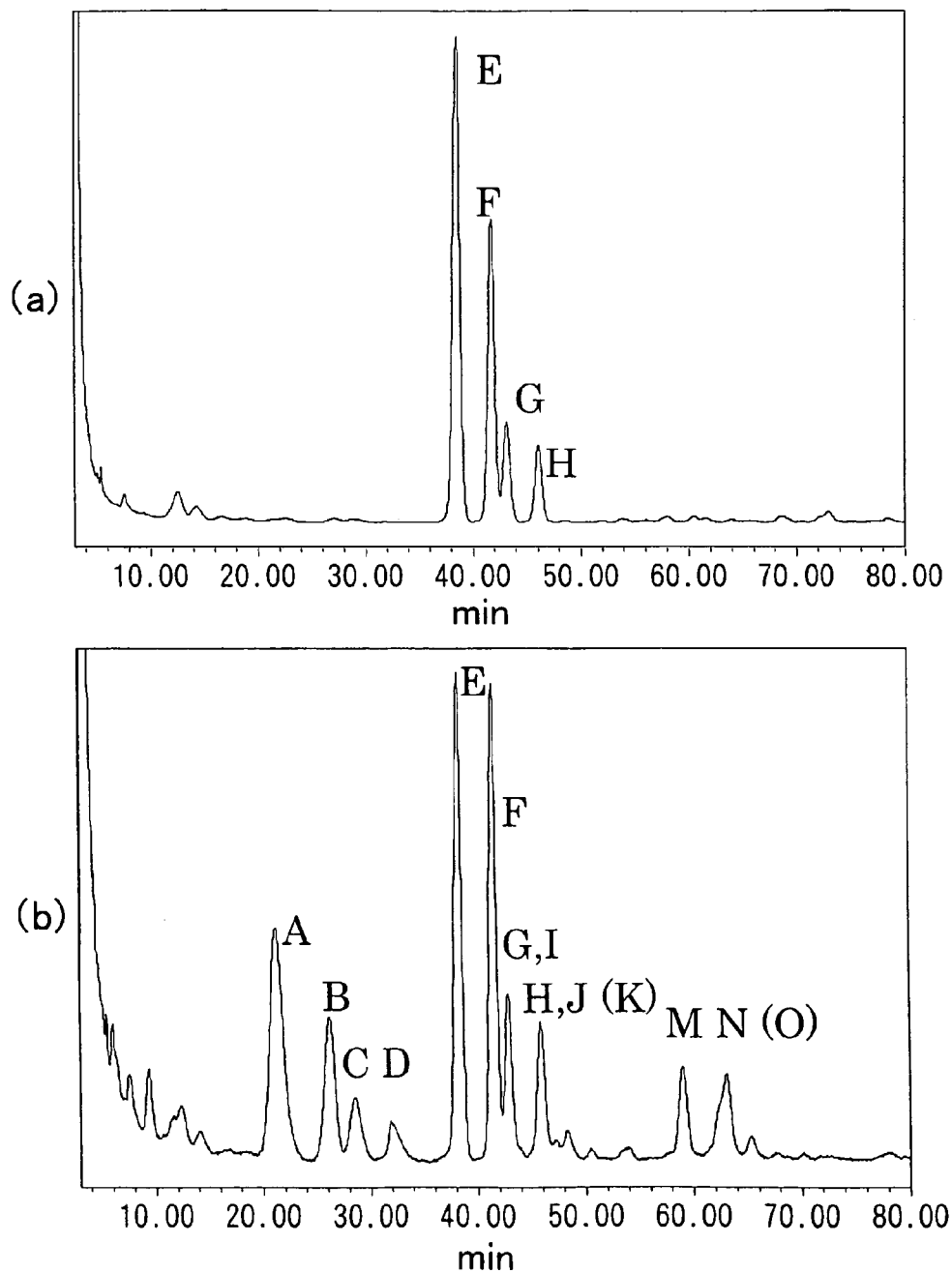
FIG. 8 is a reverse phase HPLC chromatogram of a pyridy-laminated sugar chain prepared from a CHO-derived antibody (a) and a YB2/0-derived antibody (b). It indicates that sugar chain patterns vary with different antibody-producing cells, and, specifically with the YB2/0-derived antibody, the peak group (A-D) estimated to be devoid of fucose is increased.

After pyridylaminated sugar chains were prepared for the YB2/0-derived antibody of the present invention and the CHO-derived antibody as the control sample in the method of the above Reference Example 8-1, reverse phase HPLC analysis was performed with an ODS column (Palpak Type R manufactured by TAKARA) and the chromatograms were compared. As compared to the sugar chains of the CHO-derived antibody, it was confirmed that the sugar chains of the YB2/0-derived antibody exhibited increases in peaks of sugar chains (A-D), possibly fucose-free, that eluate at 20-35 minutes (FIG. 8).

3. Analysis by Two Dimensional Mapping of Purified Pyridylaminated Sugar Chains

After pyridylaminated sugar chains were prepared for the YB2/0-derived antibody of the present invention in the method of the above Reference Example 8-1, the two dimensional mapping that combined reverse phase HPLC with an ODS column and a normal phase HPLC with an amine column (Palpak Type N manufactured by TAKARA) was performed. Specifically, the normal phase HPLC with an amine column is used to roughly fractionate the purified pyridylaminated sugar chains, and then each fraction is analyzed with the reverse phase HPLC.

Each sugar chain was identified by comparing its elution position in HPLC with those of the pyridylaminated sugar chain standards (manufactured by TAKARA, manufactured by Hohnen and manufactured by Seikagaku Kogyo; excluding K, O, and P in FIG. 9) and confirming molecular weight by TOF-MS. The relative ratio of each sugar chain identified is shown in Table 1 (differentiations of J from K and of N from O have not been performed in this Example). The structures of sugar chains are shown in FIG. 9 and FIG. 10. The result confirmed that in the YB2/0-derived antibody of the present invention, there are 30% or more of fucose-free sugar chains and there are sugar chains that have bisecting GlcNAc.

TABLE 1

| Sugar chain | Group | Relative ratio of each sugar chain | Relative ratio of each group |
|---|---|---|---|
| A | −Fuc, −Bisecting GlcNAc | 17.7% | 33.5% |
| B | | 9.9% | |
| C | | 3.9% | |
| D | | 1.9% | |
| E | +Fuc, −Bisecting GlcNAc | 22.9% | 55.2% |
| F | | 21.4% | |
| G | | 5.5% | |
| H | | 5.4% | |
| I | −Fuc, +Bisecting GlcNAc | 2.0% | 3.3% |
| J (K) | | 1.3% | |
| M | +Fuc, +Bisecting GlcNAc | 3.7% | 8.0% |
| N (O) | | 4.2% | |

Reference Example 9

Construction of Human GnTIII-Expressing Expression Vector

Figure 11:
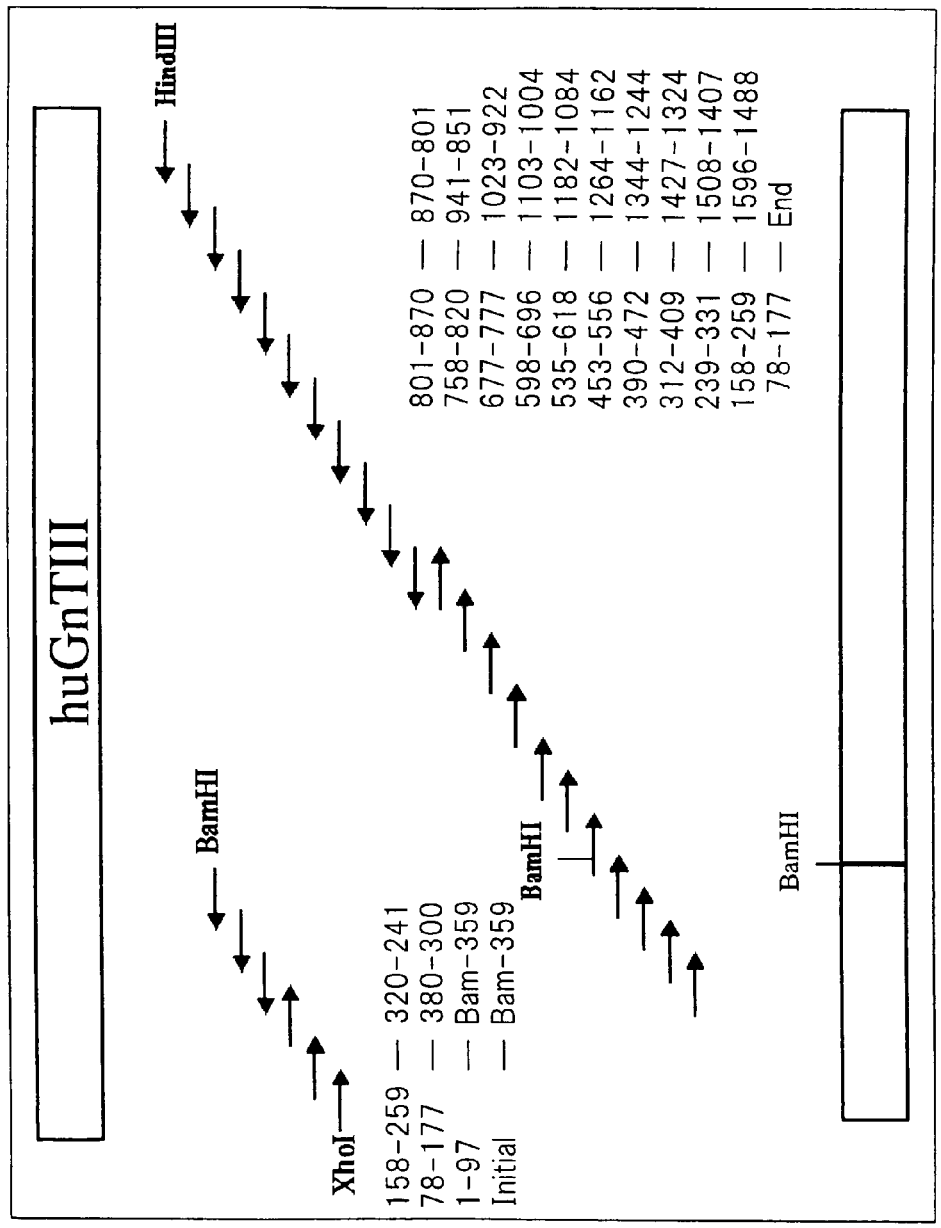
FIG. 11 shows primer sequences used for total synthesis of human GnTIII cDNA by PCR, and their combinations. PCR fragments flanking the BamHI sequence that had previously been introduced into the primer were ligated at the same sites to obtain the total sequence of human GnTIII cDNA.

The sequence of the human GnTIII gene was obtained from the NCBI database (ACCESSION D13789). The sequence was analyzed with GENETYX-SV/RC and it was found to have many repeat sequences. In order to facilitate amplification by PCR, primers that had silent mutations in several sites were designed and were obtained by synthesis using PCR. PCR used KOD polymerase (TOYOBO), double strands from the base numbers 801 to 870 as the initial templates, and the following primers sequentially to perform PCR. In the primer sequences below, capital letters indicate bases in which silent mutations have been introduced. Also, numbers indicate positions from the translation initiation site. FIG. 11 shows the position of each primer relative to the GnTIII gene.

Formula 1
(SEQ ID NOS 3-15, respectively in order of appearance)

Forward primer

| | |
|---|---|
| Initial (BamHI): | TTTCTCGAGatgagacgctacaagctctttctcatgttc |
| 1-97: | atgagacgctacaagctctttctcatgttctgtatggccggcctgtgcctcatctcttcctgcacttcttcaagaccctgtcctatgtcaccttcc |
| 78-177: | cctgtcctatgtcaccttcccAcgagaactggcctccctcagccctaacctggtgtccagcttttttctggaacaatgccccggtcacgcccaggccagc |
| 158-259: | cggtcacgcccaggccagccTgagccaggaggccctgacctgctgcgtaccccactctactcccactcgccctgctgcagccgctgccgcccagcaagg |
| 239-331: | agccgctgccgcccagcaaggcggccgaggagctccaccgggtggacttggtgctgcccgaggacaccaccgagtatttcgtgcgcaccaagg |
| 312-409: | gtatttcgtgcgcaccaaggcTggAggcgtctgcttcaaacccggcaccaagatgctggagagAccgcCTccgggacgAccggaggagaagcctgagg |
| 390-472: | AccggaggagaagcctgaggggggccaacggAtcctcggcccggcgAccaccccggtacctcctgagcgcccgggagcgcacgg |
| 453-556: | gagcgcccggagcgcacgggggggccgaggTgcAcgAcgcaagtgggtggagtgcgtgtgTctgccgcgAtggcaggacccagctgcggcgtgcccactgtgg |
| 535-618: | agctgcggcgtgcccactgtggtgcagtaTtccaacctgccTaccaaggagcggctggtgcccaggaggtgccgcgccgcgtc |
| 598-696: | agggaggtgccgcgccgcgtcatTaaTgcTatcaacgtcaaccacgagttcgacctgctggacgtgcgcttccacgagctgggcgacgtggtgacgcc |
| 677-777: | tgggcgacgtggtggacgcctttgtggtgtgcgagtccaacttcacggcttatggggagccgcggccgctcaagttccgggagatgctgaccaatggcacc |
| 758-820: | agatgctgaccaatggcaccttcgagtacatccgccacaaggtgctctatgtcttcctggacc |

Formula 2 (SEQ ID NOS 16-29, respectively in order of appearance)

Reverse primer

| | |
|---|---|
| End (HindIII): | TTTAAGCTTActagacttccgcctcgtccagttttTcc |
| 1596-1488: | ctagacttccgcctcgtccagtttTccccgAgcAggcggTcttccTtcAggaccctgtggcgccaTccTccgcAgccgtgctcctgggctcctggtagggggttgtcc |
| 1508-1407: | ggctcctggtaggggttgtccagAaggtagtggaaccggtcgtagttcttcagcaggtacttgggcgcatacatgtgctcgctggggtctgcaggcgggtac |
| 1427-1324: | ctggggtctgcaggcgggtactcTtgctgcgtgccgtcgaaccagccccggtgcggatcaggccgcggatgtagttcaggtcccgcttgtcctgtagtcacc |
| 1344-1244: | ccgcttgtcctcgtagtcaccccagcgtgggaagtcgccattctgggcggacagagcttgaagtagatgccctcgggcgtgaagcaccaggagcagtgcc |
| 1264-1162: | tgaagcaccaggagcagtgccagccggcgaagtgAaggggggctgcccagcgaccactgcaccaggatgtgTccggtgcggttctcatactgtctgaagttgg |
| 1182-1084: | ctcatactgtctgaagttgggcatggtgtagtaTtgcggcggcgcaggcggatgccgtccagcccatacactgcctgcagcatgtccaccgtgcagcc |
| 1103-1004: | agcatgtccaccgtgcagcctgacaccacctccagggtgcccggTtgcttccaAaagaaTccgtagagcgacgtgcgatgtggaaggcgaagggctcgg |
| 1023-922: | gtggaaggcgaagggctcggtccagccatcgtagagcttgaggaaCaggacgccgtcacgggccgggatctcgtccgcatcgtcaatgatgaagacgtcgtc |
| 941-851: | tcaatgatgaagacgtcgtcgggccgcaggttgcgcagccgcgagacgccgtcctgggtgaggaaggtgcgcaggtagtcgtcggcgatcc |
| 870-801: | caggtagtcgtcggcgatccaTccAtcTtgTcgTccTccAggAggAaagtggtccaggaagacatagagc |
| 380-300: | ggcggTctctccagcatcttggtgccgggtttgaagcagacgccTccAgccttggtgcgcacgaaatactcggtggtgtcc |
| 320-241: | acgaaatactcggtggtgtcctcgggcagcaccaagtccacccggtggagctcctcggccgccttgctgggcggcagcgg |
| Bam-359 | TTTggaTccgttggcccctcaggcttctcctccggTcgtcccggAggcggTctctccagcatcttgg |

As needed, amplified fragments were subjected to agarose gel electrophoresis, and fragments of interest were excised from the gel and purified, and used as the template for the subsequent PCR. As it was impossible to amplify the full-length by PCR alone, BamHI sites that had previously been introduced into the primer as silent mutation were used, and fragments flanking the sites were ligated after amplification to obtain the full-length human GnTIII gene. FIG. 15 to FIG. 19 show a comparison of a nucleotide sequence (SEQ ID NO: 30) (GnTIII ori.nuc) encoding the native human GnTIII with a nucleotide sequence (SEQ ID NO: 31) (GnTIII mut.nuc) encoding a mutant human GnTIII. In the figure, the asterisk indicates that the corresponding bases in both sequences are the same.

Human GnTIII was integrated into the XhoI/HindIII site of pcDNA3.1(Hygro-) (Invitrogen) and the sequence was confirmed.

Reference Example 10

Expression of GnTIII in CHO Cells that Express HM1.24 Antibody-DG44

Ten μg of GnTIII/pcDNA3.1(Hygro-) obtained in the above Reference Example 9 was introduced into the HM1.24 antibody-DG44-expressing CHO line by electroporation at a condition of 1.5 kV and 25 μF. Culturing was carried out in a 5% CO2 incubator at 37° C. Using the IMDM medium (Gibco) containing 10% FCS, 10 cells/100 μL/well were plated in a 96-well plate (Falcon), and cultured for two days. The medium was replaced with a 10% FCS/IMDM medium containing 400 μg/ml hygromycin and cells were selected for 1-2 weeks. The culture supernatant of the cells for which hygromycin-resistant colonies developed and growth was noted was collected, and the amount of humanized anti-HM1.24 antibody was determined by the ELISA method described in Reference Example 2.

Reference Example 11

Figure 12:
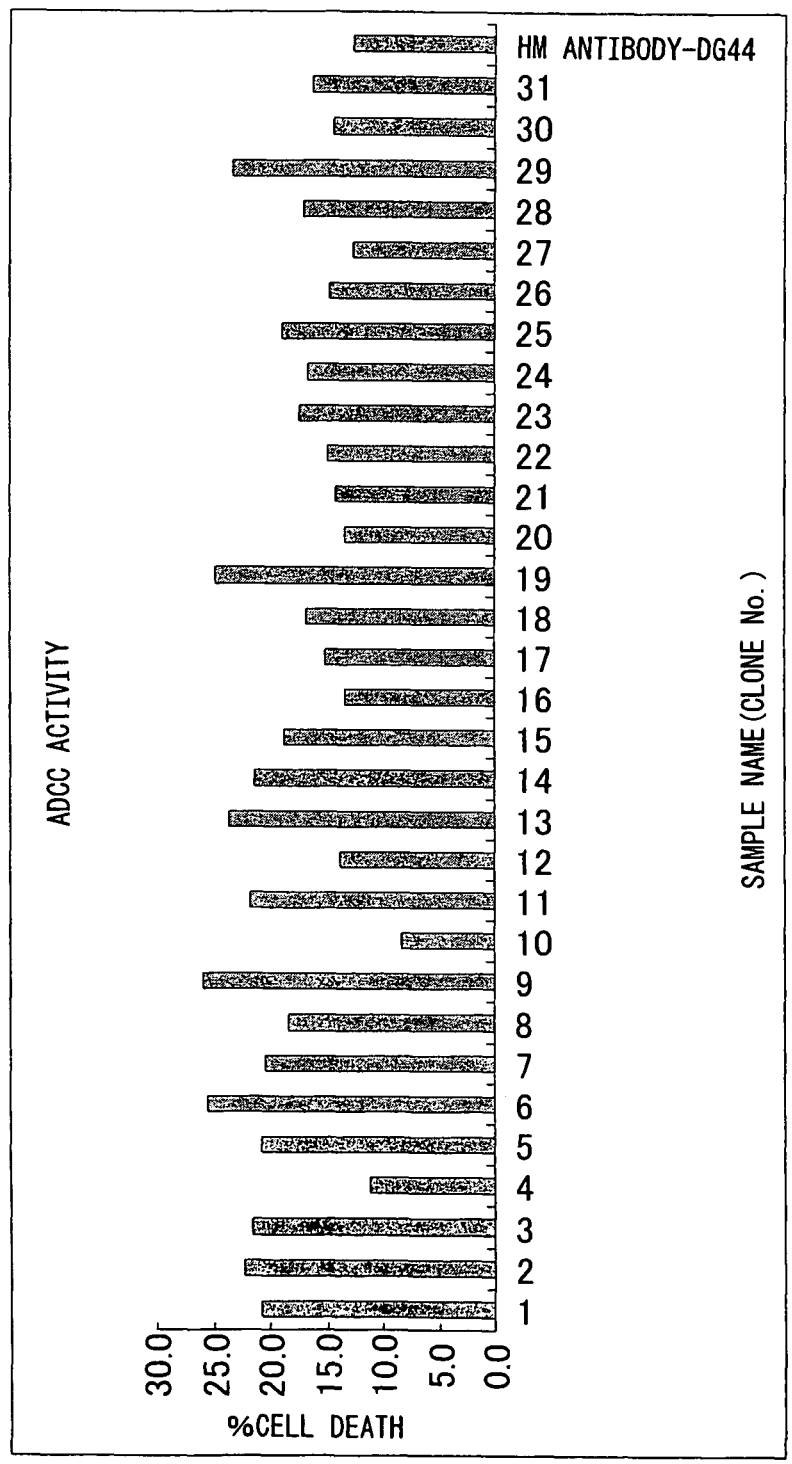
FIG. 12 shows a comparison of ADCC activity at 100 ng/ml of HM1.24 antibody-DG44 and an antibody derived from a cell line that produces a GnTIII-expressing humanized anti-HM1.24 antibody. By allowing GnTIII to be expressed, an antibody-producing cell line having an enhanced ADCC activity was obtained.

Screening by ADCC Activity of Humanized Anti-Human HM1.24 Antibody-Producing CHO Cells that Express GnTIII The culture liquids of humanized anti-HM1.24 antibody derived from humanized anti-HM1.24 antibody-producing cells (clones No. 1-31) in which GnTIII was forcefully expressed and HM1.24 antibody-DG44 were diluted with the medium to an antibody concentration of 400 ng/ml, and ADCC activity was determined using the method described in Reference Example 6 and compared (FIG. 12).

Finally, screening was carried out taking into account ADCC activity and the amount of humanized anti-HM1.24 antibody expressed and growth rate, and the clone No. 6 (57B2) was obtained.

Reference Example 12

Figure 13:
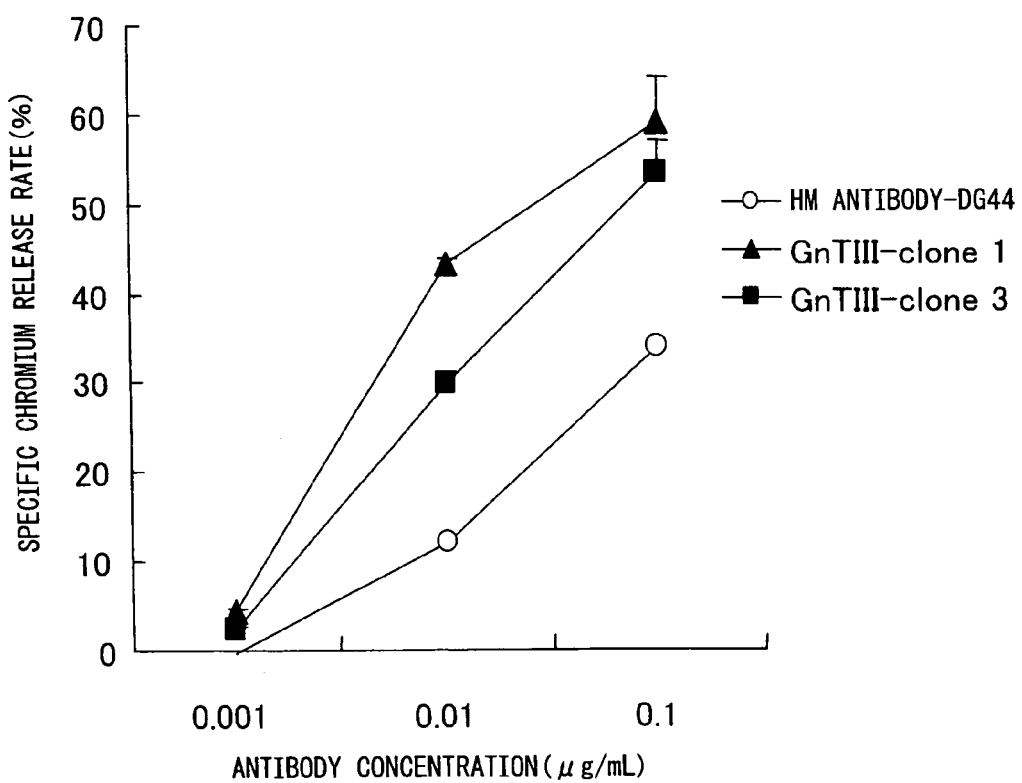
FIG. 13 shows the result of ADCC activity of human PBMC at each antibody concentration of HM1.24 antibody-DG44 and a humanized anti-HM1.24 antibody derived from GnTIII-expressing CHO cells using HM36 as the target cell and at E/T ratio=25.

Determination of ADCC Activity of Humanized Anti-HM1.24 Antibody Derived from GnTIII-Expressing CHO Cells The ADCC activity of humanized anti-HM1.24 antibody derived from humanized anti-HM1.24 antibody-producing cells in which GnTIII was forcefully expressed was determined in the method described in Reference Example 5 and the result is shown in FIG. 13. Clone No. 3 and No. 6 (57B2) were compared to HM1.24 antibody-DG44 with a result that any of the clones exhibited higher ADCC activity than HM1.24 antibody-DG44.

The invention claimed is:

1. A method for treating breast cancer or a metastatic cancer thereof, comprising administering to a subject in need of such therapy, an antibody that specifically binds to a protein having the amino acid sequence as set forth in SEQ ID NO: 2, wherein the antibody has ADCC activity, and wherein the antibody binds to the same epitope as an epitope bound by the antibody produced by the hybridoma deposited as FERM BP-5233, and wherein the breast cancer or the metastatic cancer thereof expresses the HM1.24 antigen.

2. The method according to claim 1, wherein the antibody is a chimeric antibody or a humanized antibody.

3. The method according to claim 1, wherein the antibody is a monoclonal antibody.

4. The method according to claim 3, wherein the antibody comprises a variable region containing the three light chain CDRs of the anti-HM1.24 antibody produced by the hybridoma deposited as FERM BP-5233, and a variable region containing the three heavy chain CDRs of the anti-HM1.24 antibody produced by the hybridoma deposited as FERM BP-5233.

5. The method according to claim 4, wherein the antibody comprises a constant region Cγ1 or Cγ3 of a human antibody.

6. The method according to claim 5, wherein the antibody is a chimeric antibody or a humanized antibody.

* * * * *

SEQUENCE LISTING

```
<160> NUMBER OF SEQ ID NOS: 31

<210> SEQ ID NO 1
<211> LENGTH: 1013
<212> TYPE: DNA
<213> ORGANISM: Homo sapiens
<220> FEATURE:
<221> NAME/KEY: CDS
<222> LOCATION: (23)..(562)

<400> SEQUENCE: 1
gaattcggca cgagggatct gg atg gca tct act tcg tat gac tat tgc aga        52
                        Met Ala Ser Thr Ser Tyr Asp Tyr Cys Arg
                         1               5                  10 gtg ccc atg gaa gac ggg gat aag cgc tgt aag ctt ctg ctg ggg ata        100
Val Pro Met Glu Asp Gly Asp Lys Arg Cys Lys Leu Leu Leu Gly Ile
                15                  20                  25 gga att ctg gtg ctc ctg atc atc gtg att ctg ggg gtg ccc ttg att        148
Gly Ile Leu Val Leu Leu Ile Ile Val Ile Leu Gly Val Pro Leu Ile
            30                  35                  40 atc ttc acc atc aag gcc aac agc gag gcc tgc cgg gac ggc ctt cgg        196
Ile Phe Thr Ile Lys Ala Asn Ser Glu Ala Cys Arg Asp Gly Leu Arg
        45                  50                  55 gca gtg atg gag tgt cgc aat gtc acc cat ctc ctg caa caa gag ctg        244
Ala Val Met Glu Cys Arg Asn Val Thr His Leu Leu Gln Gln Glu Leu
    60                  65                  70 acc gag gcc cag aag ggc ttt cag gat gtg gag gcc cag gcc gcc acc        292
Thr Glu Ala Gln Lys Gly Phe Gln Asp Val Glu Ala Gln Ala Ala Thr
75                  80                  85                  90 tgc aac cac act gtg atg gcc cta atg gct tcc ctg gat gca gag aag        340
```

```
        Cys Asn His Thr Val Met Ala Leu Met Ala Ser Leu Asp Ala Glu Lys
                        95                 100                 105 gcc caa gga caa aag aaa gtg gag gag ctt gag gga gag atc act aca        388
Ala Gln Gly Gln Lys Lys Val Glu Glu Leu Glu Gly Glu Ile Thr Thr
            110                 115                 120 tta aac cat aag ctt cag gac gcg tct gca gag gtg gag cga ctg aga        436
Leu Asn His Lys Leu Gln Asp Ala Ser Ala Glu Val Glu Arg Leu Arg
        125                 130                 135 aga gaa aac cag gtc tta agc gtg aga atc gcg gac aag aag tac tac        484
Arg Glu Asn Gln Val Leu Ser Val Arg Ile Ala Asp Lys Lys Tyr Tyr
140                 145                 150 ccc agc tcc cag gac tcc agc tcc gct gcg gcg ccc cag ctg ctg att        532
Pro Ser Ser Gln Asp Ser Ser Ser Ala Ala Ala Pro Gln Leu Leu Ile
155                 160                 165                 170 gtg ctg ctg ggc ctc agc gct ctg ctg cag tgagatccca ggaagctggc          582
Val Leu Leu Gly Leu Ser Ala Leu Leu Gln
                    175                 180 acatcttgga aggtccgtcc tgctcggctt ttcgcttgaa cattcccttg atctcatcag      642
ttctgagcgg gtcatggggc aacacggtta gcggggagag cacggggtag ccggagaagg      702
gcctctggag caggtctgga ggggccatgg ggcagtcctg ggtctgggga cacagtcggg      762
ttgacccagg gctgtctccc tccagagcct ccctccggac aatgagtccc cctcttgtc      822 tcccaccctg agattgggca tggggtgcgg tgtgggggc atgtgctgcc tgttgttatg      882 ggttttttttt gcggggggggg ttgcttttttt ctggggtctt tgagctccaa aaaaataaac    942
acttcctttg agggagagca caccttaaaa aaaaaaaaa aaaaaaaaa aaaaaattc         1002 gggcggccgc c                                                           1013

<210> SEQ ID NO 2
<211> LENGTH: 180
<212> TYPE: PRT
<213> ORGANISM: Homo sapiens

<400> SEQUENCE: 2

Met Ala Ser Thr Ser Tyr Asp Tyr Cys Arg Val Pro Met Glu Asp Gly
 1               5                  10                  15

Asp Lys Arg Cys Lys Leu Leu Leu Gly Ile Gly Ile Leu Val Leu Leu
                20                  25                  30

Ile Ile Val Ile Leu Gly Val Pro Leu Ile Ile Phe Thr Ile Lys Ala
            35                  40                  45

Asn Ser Glu Ala Cys Arg Asp Gly Leu Arg Ala Val Met Glu Cys Arg
        50                  55                  60

Asn Val Thr His Leu Leu Gln Gln Glu Leu Thr Glu Ala Gln Lys Gly
65                  70                  75                  80

Phe Gln Asp Val Glu Ala Gln Ala Ala Thr Cys Asn His Thr Val Met
                85                  90                  95

Ala Leu Met Ala Ser Leu Asp Ala Glu Lys Ala Gln Gly Gln Lys Lys
            100                 105                 110

Val Glu Glu Leu Glu Gly Glu Ile Thr Thr Leu Asn His Lys Leu Gln
        115                 120                 125

Asp Ala Ser Ala Glu Val Glu Arg Leu Arg Arg Glu Asn Gln Val Leu
    130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175
```

Ala Leu Leu Gln
        180

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 3
tttctcgaga tgagacgcta caagctcttt ctcatgttc                               39

<210> SEQ ID NO 4
<211> LENGTH: 97
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 4
atgagacgct acaagctctt tctcatgttc tgtatggccg gcctgtgcct catctccttc        60
ctgcacttct tcaagaccct gtcctatgtc accttcc                                 97

<210> SEQ ID NO 5
<211> LENGTH: 100
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 5
cctgtcctat gtcaccttcc cacgagaact ggcctccctc agccctaacc tggtgtccag        60 cttttctgg aacaatgccc cggtcacgcc ccaggccagc                               100

<210> SEQ ID NO 6
<211> LENGTH: 102
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 6
cggtcacgcc ccaggccagc cctgagccag gaggccctga cctgctgcgt accccactct        60
actcccactc gcccctgctg cagccgctgc cgcccagcaa gg                          102

<210> SEQ ID NO 7
<211> LENGTH: 93
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 7
agccgctgcc gcccagcaag gcggccgagg agctccaccg ggtggacttg gtgctgcccg        60
aggacaccac cgagtatttc gtgcgcacca agg                                     93

<210> SEQ ID NO 8
<211> LENGTH: 98
<212> TYPE: DNA

<213> ORGANISM: Artificial Sequence
<220> FEATURE:
<223> OTHER INFORMATION: Description of Artificial Sequence: Synthetic
      forward primer

<400> SEQUENCE: 8
gtatttcgtg cgcaccaagg ctggaggcgt ctgcttcaaa cccggcacca agatgctgga    60
gagaccgcct ccgggacgac cggaggagaa gcctgagg                            98

<210> SEQ ID NO 9
<211> LENGTH: 83
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 9
accggaggag aagcctgagg gggccaacgg atcctcggcc cggcgaccac cccggtacct    60
cctgagcgcc cgggagcgca cgg                                            83

<210> SEQ ID NO 10
<211> LENGTH: 104
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 10
gagcgcccgg gagcgcacgg ggggccgagg tgcacgacgc aagtgggtgg agtgcgtgtg    60
tctgcccgga tggcacggac ccagctgcgg cgtgcccact gtgg                    104

<210> SEQ ID NO 11
<211> LENGTH: 84
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 11
agctgcggcg tgcccactgt ggtgcagtat tccaacctgc ctaccaagga gcggctggtg    60
cccagggagg tgccgcgccg cgtc                                           84

<210> SEQ ID NO 12
<211> LENGTH: 99
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 12
agggaggtgc cgcgccgcgt cattaatgct atcaacgtca accacgagtt cgacctgctg    60
gacgtgcgct tccacgagct gggcgacgtg gtggacgcc                           99

<210> SEQ ID NO 13
<211> LENGTH: 101
<212> TYPE: DNA
<213> ORGANISM: Artificial Sequence
<220> FEATURE:
<223> OTHER INFORMATION: Description of Artificial Sequence: Synthetic
      forward primer

```
<400> SEQUENCE: 13
tgggcgacgt ggtggacgcc tttgtggtgt gcgagtccaa cttcacggct tatggggagc      60
cgcggccgct caagttccgg gagatgctga ccaatggcac c                         101

<210> SEQ ID NO 14
<211> LENGTH: 63
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 14
agatgctgac caatggcacc ttcgagtaca tccgccacaa ggtgctctat gtcttcctgg      60
acc                                                                   63

<210> SEQ ID NO 15
<211> LENGTH: 70
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 15
gctctatgtc ttcctggacc actttcctcc tggaggacga caagatggat ggatcgccga     60
cgactacctg                                                            70

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 16
tttaagctta ctagacttcc gcctcgtcca gttttcc                              37

<210> SEQ ID NO 17
<211> LENGTH: 109
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 17
ctagacttcc gcctcgtcca gttttcccccg agcaggcggt cttccttcag gaccccctgtg   60 gcgccatcct cccgcagccg tgctcctggg ctcctggtag gggttgtcc                 109

<210> SEQ ID NO 18
<211> LENGTH: 102
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 18
ggctcctggt aggggttgtc cagaaggtag tggaaccggt cgtagttctt cagcaggtac     60
ttgggcgcat acatgtgctc gctggggtct gcaggcgggt ac                        102
```

```
<210> SEQ ID NO 19
<211> LENGTH: 104
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 19
ctggggtctg caggcgggta ctcttgctgc gtgccgtcga accagccccc ggtgcggatc        60
aggccgcgga tgtagttcag gtcccgcttg tcctcgtagt cacc                       104

<210> SEQ ID NO 20
<211> LENGTH: 101
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 20
ccgcttgtcc tcgtagtcac cccagcgtgg gaagtcgcca ttctgggcgg acacgagctt        60
gaagtagatg ccctcgggcg tgaagcacca ggagcagtgc c                          101

<210> SEQ ID NO 21
<211> LENGTH: 102
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 21
tgaagcacca ggagcagtgc cagccggcga agtgaagggg gctgcccagc gaccactgca        60
ccaggatgtg tccggtgcgg ttctcatact gtctgaagtt gg                         102

<210> SEQ ID NO 22
<211> LENGTH: 99
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 22
ctcatactgt ctgaagttgg gcatggtgta gtattggcgg cggcgcaggc ggatgccgtc        60
cagcccatac actgcctgca gcatgtccac cgtgcagcc                              99

<210> SEQ ID NO 23
<211> LENGTH: 100
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 23
agcatgtcca ccgtgcagcc tgacaccacc tccagggtgc ccggttgctt ccaaaagaat        60
ccgtagagcg acgtgcgcat gtggaaggcg aagggctcgg                            100

<210> SEQ ID NO 24
<211> LENGTH: 102
<212> TYPE: DNA
<213> ORGANISM: Artificial Sequence
<220> FEATURE:
```

-continued

<223> OTHER INFORMATION: Description of Artificial Sequence: Synthetic
      reverse primer

<400> SEQUENCE: 24
gtggaaggcg aagggctcgg tccagccatc gtagagcttg aggaacagga cgccgtcacg    60
ggccgggatc tcgtccgcat cgtcaatgat gaagacgtcg tc                      102

<210> SEQ ID NO 25
<211> LENGTH: 91
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 25
tcaatgatga agacgtcgtc gggccgcagg ttgcgcagcc gcgagacgcc gtcctgggtg    60
aggaaggtgc gcaggtagtc gtcggcgatc c                                   91

<210> SEQ ID NO 26
<211> LENGTH: 70
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 26
caggtagtcg tcggcgatcc atccatcttg tcgtcctcca ggaggaaagt ggtccaggaa    60
gacatagagc                                                            70

<210> SEQ ID NO 27
<211> LENGTH: 81
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 27
ggcggtctct ccagcatctt ggtgccgggt ttgaagcaga cgcctccagc cttggtgcgc    60
acgaaatact cggtggtgtc c                                               81

<210> SEQ ID NO 28
<211> LENGTH: 80
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 28
acgaaatact cggtggtgtc ctcgggcagc accaagtcca cccgtggag ctcctcggcc     60 gccttgctgg gcggcagcgg                                                 80

<210> SEQ ID NO 29
<211> LENGTH: 68
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 29

```
tttggatccg ttggcccct caggcttctc ctccggtcgt cccggaggcg gtctctccag    60
catcttgg                                                             68

<210> SEQ ID NO 30
<211> LENGTH: 1596
<212> TYPE: DNA
<213> ORGANISM: Homo sapiens

<400> SEQUENCE: 30
atgagacgct acaagctctt tctcatgttc tgtatggccg gcctgtgcct catctccttc    60
ctgcacttct tcaagaccct gtcctatgtc accttccccc gagaactggc ctccctcagc   120
cctaacctgg tgtccagctt tttctggaac aatgccccgg tcacgcccca ggccagcccc   180
gagccaggag ccctgacct gctgcgtacc ccactctact cccactcgcc cctgctgcag   240
ccgctgccgc ccagcaaggc ggccgaggag ctccaccggg tggacttggt gctgcccgag   300
gacaccaccg agtatttcgt gcgcaccaag gccggcggcg tctgcttcaa acccggcacc   360
aagatgctgg agaggccgcc cccgggacgg ccggaggaga agcctgaggg ggccaacggc   420
tcctcggccc ggcggccacc ccggtacctc ctgagcgccc gggagcgcac gggggggccga   480 ggcgcccggc gcaagtgggt ggagtgcgtg tgcctgcccg gctggacgg acccagctgc   540 ggcgtgccca ctgtggtgca gtactccaac ctgcccacca aggagcggct ggtgcccagg   600
gaggtgccgc gccgcgtcat caacgccatc aacgtcaacc acgagttcga cctgctggac   660
gtgcgcttcc acgagctggg cgacgtggtg gacgcctttg tggtgtgcga gtccaacttc   720
acggcttatg gggagccgcg gccgctcaag ttccgggaga tgctgaccaa tggcaccttc   780
gagtacatcc gccacaaggt gctctatgtc ttcctggacc acttcccgcc cggcggccgg   840
caggacggct ggatcgccga cgactacctg cgcaccttcc tcacccagga cggcgtctcg   900
cggctgcgca acctgcggcc cgacgacgtc ttcatcattg acgatgcgga cgagatcccg   960
gcccgtgacg gcgtcctttt cctcaagctc tacgatggct ggaccgagcc cttcgccttc  1020
cacatgcgca cgtcgctcta cggcttcttc tggaagcagc cgggcaccct ggaggtggtg  1080
tcaggctgca cggtggacat gctgcaggca gtgtatgggc tggacggcat ccgcctgcgc  1140
cgccgccagt actacaccat gcccaacttc agacagtatg agaaccgcac cggccacatc  1200
ctggtgcagt ggtcgctggg cagcccctg cacttcgccg ctggcactg tcctggtgc  1260 ttcacgcccg agggcatcta cttcaagctc gtgtccgccc agaatggcga cttcccacgc  1320
tggggtgact acgaggacaa gcgggacctg aactacatcc gcggcctgat ccgcaccggg  1380
ggctggttcg acggcacgca gcaggagtac ccgcctgcag accccagcga gcacatgtat  1440
gcgcccaagt acctgctgaa gaactacgac cggttccact acctgctgga caaccccctac  1500 caggagccca ggagcacggc ggcgggcggg tggcgccaca ggggtcccga gggaaggccg  1560
cccgcccggg gcaaactgga cgaggcggaa gtctag                             1596

<210> SEQ ID NO 31
<211> LENGTH: 1596
<212> TYPE: DNA
<213> ORGANISM: Artificial Sequence
<220> FEATURE:
<223> OTHER INFORMATION: Description of Artificial Sequence: Synthetic
      mutant nucleotide sequence

<400> SEQUENCE: 31
atgagacgct acaagctctt tctcatgttc tgtatggccg gcctgtgcct catctccttc    60
ctgcacttct tcaagaccct gtcctatgtc accttccac gagaactggc ctccctcagc   120
```

```
cctaacctgg tgtccagctt tttctggaac aatgccccgg tcacgcccca ggccagccct    180
gagccaggag gccctgacct gctgcgtacc ccactctact cccactcgcc cctgctgcag    240
ccgctgccgc ccagcaaggc ggccgaggag ctccaccggg tggacttggt gctgcccgag    300
gacaccaccg agtatttcgt gcgcaccaag gctggaggcg tctgcttcaa acccggcacc    360
aagatgctgg agagaccgcc tccgggacga ccggaggaga agcctgaggg ggccaacgga    420
tcctcggccc ggcgaccacc ccggtacctc ctgagcgccc gggagcgcac gggggccga    480
ggtgcacgac gcaagtgggt ggagtgcgtg tgtctgcccg gatggcacgg acccagctgc    540
ggcgtgccca ctgtggtgca gtattccaac ctgcctacca aggagcggct ggtgcccagg    600
gaggtgccgc gccgcgtcat taatgctatc aacgtcaacc acgagttcga cctgctggac    660
gtgcgcttcc acgagctggg cgacgtggtg gacgcctttg tggtgtgcga gtccaacttc    720
acggcttatg gggagccgcg gccgctcaag ttcggggaga tgctgaccaa tggcaccttc    780
gagtacatcc gccacaaggt gctctatgtc ttcctggacc actttcctcc tggaggacga    840
caagatggat ggatcgccga cgactacctg cgcaccttcc tcacccagga cggcgtctcg    900
cggctgcgca acctgcggcc cgacgacgtc ttcatcattg acgatgcgga cgagatcccg    960
gcccgtgacg gcgtcctgtt cctcaagctc tacgatggct ggaccgagcc cttcgccttc   1020
cacatgcgca cgtcgctcta cggattcttt tggaagcaac cgggcaccct ggaggtggtg   1080
tcaggctgca cggtggacat gctgcaggca gtgtatgggc tggacggcat ccgcctgcgc   1140
cgccgccaat actacaccat gcccaacttc agacagtatg agaaccgcac cggacacatc   1200
ctggtgcagt ggtcgctggg cagccccctt cacttcgccg gctggcactg ctcctggtgc   1260
ttcacgcccg agggcatcta cttcaagctc gtgtccgccc agaatggcga cttcccacgc   1320
tggggtgact acgaggacaa gcgggacctg aactacatcc gcggcctgat ccgcaccggg   1380
ggctggttcg acggcacgca gcaagagtac ccgcctgcag accccagcga gcacatgtat   1440
gcgcccaagt acctgctgaa gaactacgac cggttccact accttctgga caaccctac    1500
caggagccca ggagcacggc tgcgggagga tggcgccaca ggggtcctga aggaagaccg   1560
cctgctcggg gaaaactgga cgaggcggaa gtctag                             1596
```